US010849936B2

(12) United States Patent
Hamilton et al.

(10) Patent No.: US 10,849,936 B2
(45) Date of Patent: Dec. 1, 2020

(54) COMPOSITIONS AND METHODS FOR *C. DIFFICILE* TREATMENT

(71) Applicant: REGENTS OF THE UNIVERSITY OF MINNESOTA, Minneapolis, MN (US)

(72) Inventors: Matthew J. Hamilton, Burnsville, MN (US); Alexander Khoruts, Golden Valley, MN (US); Michael J. Sadowsky, Roseville, MN (US); Christopher M. Staley, Saint Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 127 days.

(21) Appl. No.: 16/313,791

(22) PCT Filed: Jul. 3, 2017

(86) PCT No.: PCT/US2017/040591
§ 371 (c)(1),
(2) Date: Dec. 27, 2018

(87) PCT Pub. No.: WO2018/006088
PCT Pub. Date: Jan. 4, 2018

(65) Prior Publication Data
US 2019/0247445 A1 Aug. 15, 2019

Related U.S. Application Data

(60) Provisional application No. 62/357,814, filed on Jul. 1, 2016.

(51) Int. Cl.
*A61K 35/74* (2015.01)
*A61K 9/00* (2006.01)
*A61P 31/04* (2006.01)
*A61K 9/19* (2006.01)
*A61K 31/43* (2006.01)
*A61K 9/16* (2006.01)
*A61K 9/20* (2006.01)
*A01N 1/02* (2006.01)

(52) U.S. Cl.
CPC ............... *A61K 35/74* (2013.01); *A01N 1/02* (2013.01); *A61K 9/0053* (2013.01); *A61K 9/1623* (2013.01); *A61K 9/1682* (2013.01); *A61K 9/19* (2013.01); *A61K 9/2095* (2013.01); *A61K 31/43* (2013.01); *A61P 31/04* (2018.01)

(58) Field of Classification Search
CPC ........ A61K 35/74; A61K 9/0053; A61K 9/19; A61K 2035/115; A61K 9/1682; A61K 9/2095; A61K 9/1623; A61K 31/43; A61K 45/06; A61K 38/14; A61P 31/04; A01N 1/02
See application file for complete search history.

(56) References Cited

U.S. PATENT DOCUMENTS 9,308,226 B2 4/2016 Borody
2014/0147425 A1 5/2014 Henn et al.
2015/0374761 A1 12/2015 Sadowsky et al.

FOREIGN PATENT DOCUMENTS

WO WO 2012/016287 A2 2/2012
WO WO 2012/122478 A1 9/2012
WO WO 2014/152484 A1 9/2014

OTHER PUBLICATIONS

Youngster et al., JAMA, 2014, vol. 312, No. 17, p. 1772-1778, published online on Oct. 11, 2014.*
Aronesty, "Comparison of Sequencing Utility Programs," *The Open Bioinformatics Journal* 7:1-8 (2013).
Bakken, "Fecal bacteriotherapy for recurrent *Clostridium difficile* infection," *Anaerobe* 15:285-289 (2009).
Cangelosi et al., "Dead or Alive: Molecular Assessment of Microbial Viability," *Applied and Environmental Microbiology* 80:5884-5891 (2014).
Garey et al., "Meta-analysis to assess risk factors for recurrent *Clostridium difficile* infection," *Journal of Hospital Infection* 70:298-304 (2008).
Claesson et al., "Comparison of two next-generation sequencing technologies for resolving highly complex microbiota composition using tandem variable 16S rRNA gene regions," *Nucleic Acids Research* 38:1-13 (2010).
Chang et al., "Decreased Diversity of the Fecal Microbiome in Recurrent *Clostridium difficile*-Associated Diarrhea," *The Journal of Infectious Diseases* 197:435-438 (2008).
Cole et al., "The Ribosomal Database Project: improved alignments and new tools for rRNA analysis," *Nucleic Acids Research* 37:D141-D145 (2009).
Edgar et al., "UCHIME improves sensitivity and speed of chimera detection," *Bioinformatics* 27:2194-2200 (2011).
Eiseman et al., "Fecal enema as an adjunct in the treatment of pseudomembranous enterocolitis," *Surgery*, 44(5):854-859 (1958).
Gihring et al., "Massively parallel rRNA gene sequencing exacerbates the potential for biased community diversity comparisons due to variable library sizes," *Environmental Microbiol* 14:285-290 (2012).
Hamilton et al., "Standardized Frozen Preparation for Transportation of Fecal Microbiota for Recurrent *Clostridium difficile* Infection," *American Journal Gastroenterology* 107:761-767 (2012).
Hamilton et al., "High-throughput DNA sequence analysis reveals stable engraftment of gut microbiota following transplantation of previously frozen fecal bacteria," *Gut Microbes* 4:125-135 (2013).

(Continued)

*Primary Examiner* — Kade Ariani
(74) *Attorney, Agent, or Firm* — Arnold & Porter Kaye Scholer LLP

(57) ABSTRACT

The present disclosure provides compositions and methods for treating *Clostridium difficile* infection (CDI) including primary and recurrent CDI. In particular, the compositions and methods described herein are capable of achieving a CDI clearance rate of at least 80% through a single oral dose of a pharmaceutical composition comprising a freeze-dried fecal microbiota preparation.

20 Claims, 10 Drawing Sheets

(56) References Cited

OTHER PUBLICATIONS

Hu et al., "Prospective Derivation and Validation of a Clinical Prediction Rule for Recurrent *Clostridium difficile* Infection," *Gastroenterology* 136:1206-1214 (2009).
Huse et al., "Ironing out the wrinkles in the rare biosphere through improved OUT clustering," *Environmental Microbiology* 12:1889-1898 (2010).
Issa et al., "Impact of *Clostridium difficile* on Inflammatory Bowel Disease," *Clinical Gastroenterology and Hepatology* (2007) 5:345-351.
Issa et al., "*Clostridium difficile* and Inflammatory Bowel Disease," *Inflamm Bowel Dis* 14:1432-1442.
Kelly et al., "*Clostridium difficile*—More Difficult Than Ever," *The New England Journal Medicine* 359:1932-1940 (2008).
Khoruts et al., "Therapeutic transplantation of the distal gut microbiota," *Mucosal Immunol* 4:4-7 (2011).
Khoruts et al., "Changes in the Composition of the Human Fecal Microbiome After Bacteriotherapy for Recurrent *Clostridium difficile*-associated Diarrhea," *Gastroenterol* 44:354-360 (2010).
Khoruts et al., "Understanding the mechanisms of faecal microbiota transplantation," *Nat rev Gastroenterol Hepatol* 13:508-516 (2016).
Knights et al., "Bayesian community-wide culture-independent microbial source tracking," *Nature Methods* 8:761-763 (2011).
Lin et al., "Twelve Week Storage Trail of Microbial Viability in Lyophilized and Frozen Fecal Microbiota Preparations," *Gastroenterology* p. S962 (2015).
Louie et al., "Fidaxomicin versus Vancomycin for *Clostridium difficile* Infection," *The New England Journal Medicine* 364:422-431 (2011).
McDonald et al., "Clostridium difficile Infection in Patients Discharged from US Short-stay Hospital, 1996-2003[1]" *Emerging Infectious Diseases* 12:40915 (2006).
Peterson et al., "Detection of Toxigenic *Clostridium difficile* in Stool Samples by Real-Time Polymerase Chain Reaction for the Diagnosis of *C. difficile*-Associated Diarrhea," *Clinical Infectious Diseases* 45:1152-1160 (2007).
Pepin et al., "Management and Outcomes of a First Recurrence of *Clostridium difficile*-Associated Disease in Quebec, Canada," *Clinical Infectious Diseases* 42:758-764 (2006).
Pruesse et al., "SILVA: a comprehensive online resource for quality checked and aligned ribosomal RNA sequence data compatible with ARB," *Nucleic Acids Research* 35:7188-7196 (2007).
Rodemann et al., "Incidence of *Clostridium difficile* Infection in Inflammatory Bowel Disease," *Clinical Gastroenterology and Hepatology* 5:339-344 (2007).
Schloss et al., "Introducing mothur: Open-Source Platform-Independent, Community-Supported Software for Describing and Comparing Microbial Communities," *Applied and Environmental Microbiology* 75-7537-7541 (2009).
Seekatz et al., "Recovery of the Gut Microbiome following Fecal Microbiota Transplantation," mbio.asm.org 5:1-9 (2014).
Shahinas et al., "Toward an Understanding of Changes in Diversity Associated with Fecal Microbiome Transportation Based on 16S rRNA Gene Deep Sequencing," mbio.asm.org 3:1-10 (2012).
Shanker et al., "Species and genus level resolution analysis of gut microbiota in *Clostridium difficile* patients following fecal microbiota transplantation," *Microbiome* 2:1-10 (2014).
Shannon et al., "The Mathematical Theory of Communication," *The University of Illinois Press Urbana* (1949).
Sogin et al., "Microbial diversity in the deep sea and the underexplored rare biosphere" *Proceed National Academy Science USA* 103-12115. 12120 (2006).
Staley et al., "Evaluation of water sampling methodologies for amplicon-based characterization of bacterial community structure," *J Microbiol Methods* 114:43-50 (2015).
Stocks, "Mechanism and Use of the Commercially Available Viability Stain, BacLight," *Cytometry Part 1* 61:189-195 (2004).
Surawicz, "Reining in Recurrent *Clostridium difficile* Infection—Who's a Risk?" *Gastroenterology* 136:1152-1154 (2009).
Weingarden et al., "Microbiota transplantation restores fecal bile and composition in recurrent Clostridium difficile infection," *Am J. Physiol Gastrointest Liver Physiol* 306:G310-G319 (2014).
Weingarden et al., "Dynamic changes in short- and long-term bacterial composition following fecal microbiota transplantation for recurrent *Clostridium difficile* infection," *Microbiome* 3:1-8 (2015).
Van Nood et al., "Struggling with Recurrent *Clostridium Difficile* Infections: IS Donor Faeces the Solution?" *Eurosurveillance* 14:1-6 (2009).
Van Nood et al., "Duodenal Infusion of Donor Feces for Recurrent *Clostridium difficile*," *The New England Journal of Medicine* 368:407-415 (2013).

\* cited by examiner

COMPOSITIONS AND METHODS FOR *C. DIFFICILE* TREATMENT

CROSS-REFERENCE TO RELATED APPLICATIONS

This application is a U.S. National Stage of International Application No. PCT/US2017/040591, filed Jul. 3, 2017, which claims priority to U.S. Provisional Application No. 62/357,814, filed Jul. 1, 2016, both of which are herein incorporated by reference in their entireties.

FIELD OF THE INVENTION

The present disclosure generally relates to medicine and gastroenterology, pharmacology, and microbiology. In particular, this application provides methods for treating *Clostridium* infection (CDI) that cannot be completely cleared with antibiotics alone.

BACKGROUND OF THE INVENTION

Widespread usage of antimicrobial drugs over many decades in medicine and agriculture has resulted in emergence of increasing numbers of antibiotic-resistant pathogens, which constitute one of the most urgent growing threats in modern healthcare. In addition, antibiotics increase vulnerability to infections by lowering colonization resistance that is normally provided by the host's own microbiota. Therefore, more targeted treatments against pathogens that can spare the host microbiota and/or restorative treatments that can recover the normal host microbiota composition is desired.

The syndrome of recurrent *Clostridium difficile* infection (R-CDI) is a common clinical challenge that captures the essential pitfalls of reliance on broad-spectrum antibiotics for treatment. The standard antibiotics for this infection, e.g., metronidazole and vancomycin, suppress gut microbiota leading to a disruption of normal microbial community structure and a decrease in overall microbial diversity. CDI reoccurs after cessation of antibiotic therapy, when the loss of protective microbiota and lack of secondary bile acids allow *C. difficile* spore germination, expansion of vegetative forms of *C. difficile* bacteria and production of endotoxins.

Recurrent CDI is one of the most difficult and increasingly common challenges associated with CDI (Surawicz, Gastroenterology 2009; 136:1152-4). An initial incidence of CDI can be followed by a relapse within 30 days in about 20-30% of cases (Kelly and LaMont. N Engl J Med 2008; 359:1932-40, Louie et al. N Engl J Med 2011; 364:422-31, Pepin et al. Clin Infect Dis 2006; 42:758-64), and the risk of recurrence doubles after two or more occurrences (McDonald et al. Emerg Infect Dis 2006; 12:40915). Older age, intercurrent antibiotic use for non-*C. difficile* indications, renal insufficiency, immune deficiency, and antacid medications, are some of the known risk factors for recurrent CDI (Surawicz, Gastroenterology 2009; 136:1152-4, Garey et al. J Hosp Infect 2008; 70:298-304). The presence of three clinical criteria: age>65 years, severe disease, and continued use of antibiotics after treating the initial CDI episode, are predictive of an almost 90% relapse rate (Hu et al. Gastroenterology 2009; 136:1206-14). CDI also commonly complicates management of inflammatory bowel disease (IBD), which has recently been recognized as an additional independent risk factor for CDI infection (Issa et al. Clin Gastroenterol Hepatol 2007; 5:345-51, Rodemann et al. Clin Gastroenterol Hepatol 2007; 5:339-4415). CDI in patients with underlying IBD is associated with increased severity of colitis and higher rates of recurrence and colectomy (Issa et al. Inflamm Bowel Dis 2008; 14:1432-42).

It has been suggested that the presence of normal, healthy, intestinal microbiota (normal gut microorganisms) offers protection against CDI. Conversely, severe disruption of normal intestinal microbiota by use of antibiotics, including metronidazole and vancomycin that are used to treat CDI, is likely one of the major reason for its recurrence. Chang and colleagues used 16S rDNA sequencing to analyze the fecal microbiota of seven patients with initial and recurrent CDI (Chang et al. J Infect Dis 2008; 197:435-8). Their report asserts that bacterial species diversity was reduced in all patients compared to nominal control subjects. Similarly, Khoruts and colleagues reported marked dysbiosis in patients with CDI as compared to controls using TRFLP analyses of fecal microbiota (Khoruts et al. J Clin Gastroenterol. 2010; 44:354-60). The greatest reduction in species diversity, however, was found in the three patients with recurrent CDI and disruption of their gut microbiota was evident at the phylum level—with marked reduction in Bacteriodetes, normally one of the two dominant phyla in the colon. Instead, the gut microbiota in these patients were dominated by members of the *Proteobacteria* and *Verrucomicrobia* phyla, which usually are only minor constituents of the colon microbiota.

Fecal microbiota transplantation (FMT), also known as 'fecal bacteriotherapy,' represents the one therapeutic protocol that allows the fastest reconstitution of a normal composition and functional gut microbial community. For many decades, FMT has been offered by select centers across the world, typically as an option of last resort for patients with recurrent *Clostridium difficile* infection (CDI). A commonly cited early report for FMT was by Eiseman and colleagues who in 1958 described the use of fecal enemas for patients who likely had severe or fulminant form of pseudomembranous colitis (Eiseman et al. Surgery 1958; 44:854-9). Since this time, well over 500 cases have been reported as individual case reports, small case series, or clinical trials with a ~90% cumulative success rate in clearing recurrent CDI, without any noted adverse events. The history and general methodology used for FMT have been described in several recent reviews (Bakken. Anaerobe 2009; 15:285-9, van Nood et al. Euro Surveill 2009; 14, Khoruts and Sadowsky. Mucosal Immunol 2011; 4:4-7, Khoruts and Sadowsky Nat Rev Gastroenterol Hepatol. 2016:doi: 10.1038/nrgastro.2016.98).

A recent randomized, controlled clinical study has confirmed the remarkable efficacy of this therapeutic approach (van Nood et al., 2013, N Engl J Med, 368:407-15). However, despite the long and successful track record, as well as great clinical need, the availability of the procedure for many patients remains very limited.

Currently, FMT is administered by several routes including infusion of human microbiota in the form of homogenized stool, extracts of homogenized stool, or cultured stool components through a colonoscope, an enema, or via a nasojejunal tube. Although Youngster et al. JAMA 2014 asserts that encapsulated, frozen microbiota can be delivered orally and results in successful treatment of R-CDI, the practicality of this preparation is limited by esthetic, storage, and shelf-life issues. Against this backdrop, the present disclosure provides a next-generation form of capsule FMT using a freeze-dried preparation of microbiota that could tolerate a range of temperatures to allow ease of handling, administration, and storage. The methods and compositions described here satisfy several conditions: (1) the freeze-drying procedure preserve the viability of the majority of the entire taxonomic spectrum of microbiota, (2) the resulting material have physicochemical properties that enable standardized encapsulation, (3) the encapsulation procedure does not compromise the viability of microbiota, and (4) the microbiota engrafts into the colon and successfully treat R-CDI. Furthermore, the instant disclosure achieves high CDI clearance rate in a single dose.

SUMMARY OF THE INVENTION

The present disclosure comprises methods for treating *Clostridium difficile* infections (CDI) in subjects in need thereof. In some aspects, the present disclosure includes methods for treating a primary CDI. In other aspects, the present disclosure includes methods for treating a recurrent CDI that cannot be cleared with antibiotics alone.

More particularly, in an aspect, the method of the present disclosure comprises orally administrating to a subject in need thereof a single dose of a pharmaceutical composition comprising a freeze-dried fecal microbrobe preparation, where the single dose is capable of achieving a CDI clearance rate of at least 80% in a population of the subjects receiving the single dose of the pharmaceutical composition.

A further aspect of the present disclosure is that the method of the present disclosure comprises orally administrating to a subject in need thereof a single dose of a pharmaceutical composition comprising a freeze-dried fecal microbe preparation, where the single dose is capable of achieving at least 80% CDI clearance rate.

BRIEF DESCRIPTION OF THE DRAWINGS

Corresponding reference characters indicate corresponding parts throughout the several views. The example(s) set out herein illustrate(s) several aspects of the present disclosure but should not be construed as limiting the scope of the present disclosure in any manner.

DETAILED DESCRIPTION

Figure 1A:
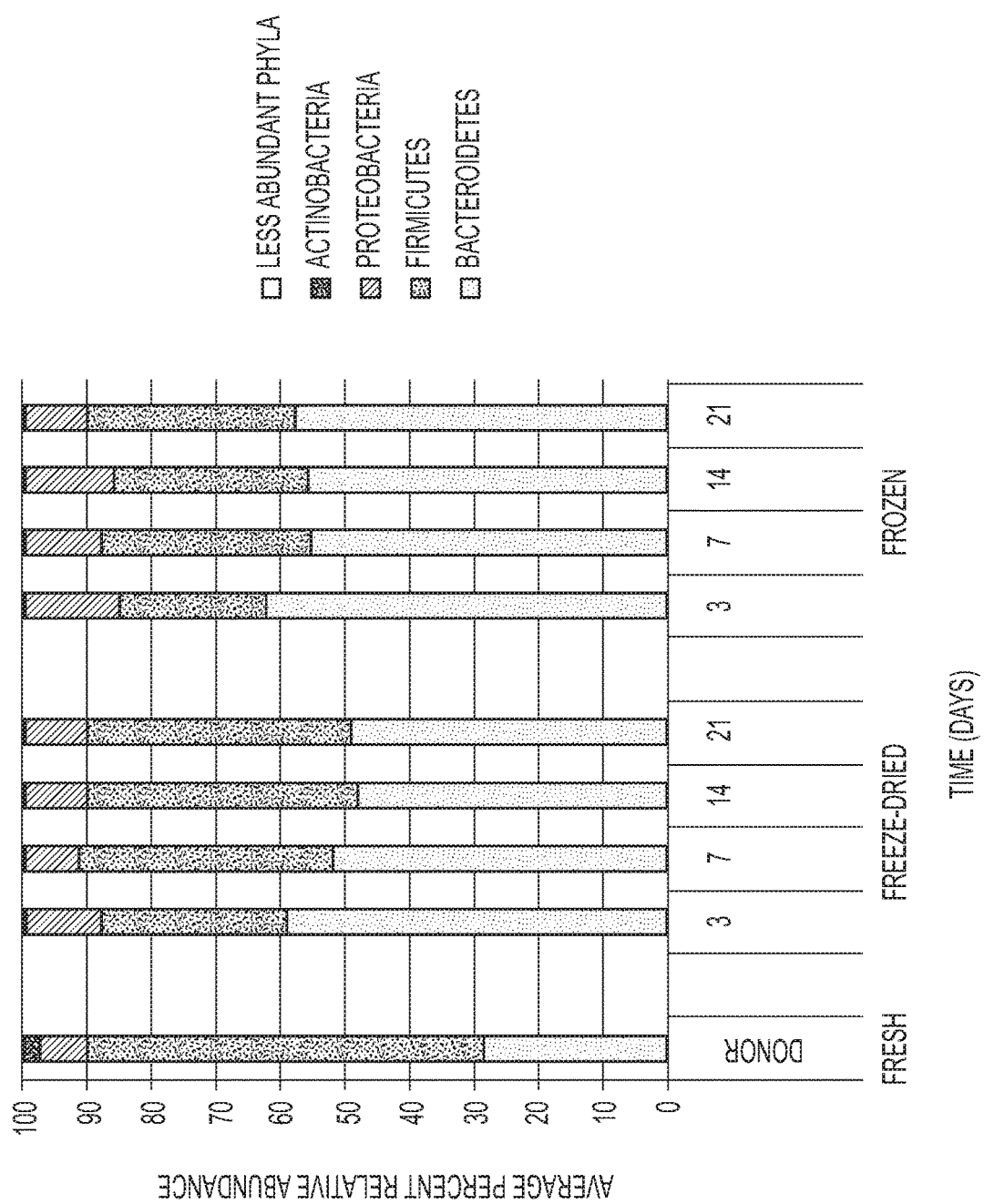
FIG. 1A shows a distribution of phyla among all mouse fecal pellets and donor samples, without rarefication in accordance with Example 2 of the present disclosure.

This description is not intended to be a detailed catalog of all the different ways in which the disclosure may be implemented, or all the features that may be added to the instant disclosure. For example, features illustrated with respect to one aspect may be incorporated into other aspects, and features illustrated with respect to a particular aspect may be deleted from that aspect. Thus, the disclosure contemplates that in some aspects of the disclosure, any feature or combination of features set forth herein can be excluded or omitted. In addition, numerous variations and additions to the various aspects suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular aspects of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects only and is not intended to be limiting of the disclosure.

All publications, patent applications, patents and other references cited herein are incorporated by reference in their entireties.

Unless the context indicates otherwise, it is specifically intended that the various features of the disclosure described herein can be used in any combination. Moreover, the present disclosure also contemplates that in some aspects of the disclosure, any feature or combination of features set forth herein can be excluded or omitted.

Methods disclosed herein can comprise one or more steps or actions for achieving the described method. The method steps and/or actions may be interchanged with one another without departing from the scope of the present invention. In other words, unless a specific order of steps or actions is required for proper operation of the aspect, the order and/or use of specific steps and/or actions may be modified without departing from the scope of the present invention. For example, the steps may be conducted in any feasible order. And, as appropriate, any combination of two or more steps may be conducted simultaneously.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

The terms "about," "approximately," and "substantially" as used herein when referring to a measurable value such as a percentage, cell count, volume and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, "CDI clearance" refers to a lack of spontaneous relapse of diarrheal symptoms and absence of *C. difficile* toxin B in stools within two months of administrating a therapeutic agent.

As used herein, "absence of *C. difficile* toxin B" refers to the absence of detectable *C. difficile* toxin B DNA tested by PCR. See e.g. Peterson et al. Clin. Infect. Dis. 2007; 45:1152-60.

As used herein, "lyophilization" or "freeze drying" refers to the process of drying a material by first freezing it and then encouraging the ice within it to sublimate in a vacuum environment.

As used herein, a "cryoprotectant" refers to a substance that is added to a formulation in order to protect an active ingredient during freezing, e.g. microbial cells.

As used herein, a "lyoprotectant" refers to a substance that is added to a formulation in order to protect an active ingredient during the drying stage of a Lyophilization (also known as freeze-drying) process.

As used herein, the term "ambient temperature" refers to the temperature of the surrounding environment, and more specifically, the temperature of the surrounding air. The term "room temperature" refers to the indoor temperature of a temperature-controlled building, which is approximately between 15° C. (59° F.) and 22° C. (72° F.).

As used herein, "fecal bacteria" refers to bacteria that can be found in fecal matter.

As used herein, "fecal microbe" refers to one or more microbes that can be found in fecal matter.

As used herein, a "microbiota" and "flora" refer to a community of microbes that live in or on a subject's body, both sustainably and transiently, including eukaryotes, archaea, bacteria, and viruses (including bacterial viruses (i.e., phage)). A "fecal microbiota" or "fecal microbiota preparation" refers to a community of microbes present in a subject's feces. A non-selected fecal microbiota refers to a community or mixture of fecal microbes derived from a donor's fecal sample without selection and substantially resembling microbial constituents and population structure found in such fecal sample.

As used herein, the term "non-floral fecal material" refers to components of feces that are not microbial in nature. For example, non-floral fecal material includes, without limitation, undigested fiber or host cell debris.

As used herein, "viable" means possessing an intact cell membrane. Here, the viability of bacterial populations is monitored as a function of the membrane integrity of the cell. Cells with a compromised membrane are considered to be dead or dying, whereas cells with an intact membrane are considered live. For example, SYTO 9 and propidium iodide are used to stain and differentiate live and dead bacteria. See Stocks, *Cytometry A.* 2004 October; 61(2):189-95. Cell viability can also be evaluated via molecular viability analyses, e.g., a PCR-based approach, which can differentiate nucleic acids associated with viable cells from those associated with inactivated cells. See Cangelosi and Mescheke, *Appl Environ Microbiol.* 2014 October; 80(19): 5884-5891.

As used herein, "isolated" or "purified" refers to a bacterium or other entity or substance that has been (1) separated from at least some of the components with which it was associated when initially produced (whether in nature or in an experimental setting), and/or (2) produced, prepared, purified, and/or manufactured by the hand of man. Isolated or purified bacteria can be separated from at least about 10%, about 20%, about 30%, about 40%, about 50%, about 60%, about 70%, about 80%, about 90%, or more of the other components with which they were initially associated.

As used herein, the terms "pathogen" and "pathogenic" in reference to a bacterium or any other organism or entity includes any such organism or entity that is capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, "subject" refers to any animal subject including humans, laboratory animals (e.g., primates, rats, mice), livestock (e.g., cows, sheep, goats, pigs, turkeys, chickens), and household pets (e.g., dogs, cats, rodents, etc.). The subject or patient may be healthy, or may be suffering from an infection due to a gastrointestinal pathogen or may be at risk of developing or transmitting to others an infection due to a gastrointestinal pathogen.

As used herein, "Shannon Diversity Index" refers to a diversity index that accounts for abundance and evenness of species present in a given community using the formula $H=-\Sigma_{i=1}^{R} p_i \ln p_i$, where H is Shannon Diversity Index, R is the total number of species in the community, and $p_i$ is the proportion of R made up of the ith species. Higher values indicate diverse and equally distributed communities, and a value of 0 indicates only one species is present in a given community. For further reference, see Shannon and Weaver, (1949) *The mathematical theory of communication.* The University of Illinois Press, Urbana. 117 pp.

As used herein, "antibiotic" refers to a substance that is used to treat and/or prevent bacterial infection by killing bacteria, inhibiting the growth of bacteria, or reducing the viability of bacteria.

As used herein, "treatment" or "treating," with respect to a condition or a disease, is an approach for obtaining beneficial or desired results including preferably clinical results after a condition or a disease manifests in a patient. Beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, prolonging survival, and any combination thereof. Likewise, for purposes of this disclosure, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, prolonging survival, and any combination thereof.

As used herein, "prevention" or "preventing," with respect to a condition or a disease, is an approach for reducing the risk of developing a condition or a disease before it manifests in a patient. Prevention approaches include, but are not limited to: identifying a disease at its earliest stage so that prompt and appropriate management can be initiated, protecting a tissue prone to a condition or a disease prior to its manifestation, reducing or minimizing the consequences of a disease, and a combination thereof.

As used herein, "therapeutically effective amount" or "pharmaceutically active dose" refers to an amount of a composition which is effective in treating the named disease, disorder or condition.

As used herein, "a single dose of a pharmaceutical composition" refers to providing a therapeutically effective amount of a composition in a single administration.

As used herein, "alpha diversity" refers to the mean species diversity at a local scale or a specific habitat and is determined by the number of species.

As used herein, "dysbiosis" refers to a microbial imbalance or maladaptation inside the digestive tract.

An aspect of the disclosure includes a method for treating a CDI in a subject in need thereof. In some aspects, a method for treating a primary CDI in a subject in need thereof is provided. In certain aspects, a method for treating a recurrent CDI in a subject in need thereof is provided. In another aspect, this disclosure provides a method for preventing a CDI in a subject in need thereof.

In an aspect, a method of the present disclosure comprises orally administrating to a subject in need thereof a single dose of a pharmaceutical composition comprising a freeze-dried fecal microbe preparation, where the single dose is capable of achieving a CDI clearance rate of at least 80% in a population of the subjects receiving the single dose of the pharmaceutical composition. In another aspect, a single dose of the pharmaceutical composition may be capable of achieving a CDI clearance rate of at least 60% in a population of the subjects receiving the single dose of the pharmaceutical composition. In certain aspects, a single dose of the pharmaceutical composition may be capable of achieving a CDI clearance rate of at least 50%, at least 55%, at least 60%, at least 65%, at least 70%, or at least 75% in a population of the subjects receiving the single dose of the pharmaceutical composition. In certain aspects, a single dose of the pharmaceutical composition may be capable of achieving a CDI clearance rate of at least 85%, at least 90%, at least 92%, at least 94%, at least 96%, at least 98%, or at least 99% in a population of the subjects receiving the single dose of the pharmaceutical composition. In another aspect, a single dose of the pharmaceutical composition may be capable of achieving a CDI clearance rate of between 50 and 55%, between 55 and 60%, between 60 and 65%, between 65 and 70%, between 70 and 75%, between 75 and 80%, between 80 and 85%, between 85 and 90%, between 90 and 95%, between 95 and 100%, in a population of the subjects receiving the single dose of the pharmaceutical composition. In an aspect, within the first two weeks from orally administrating a single dose of the pharmaceutical composition of the present application, the subject experience little or no bowel movement irregularity, bloating, or flatulence.

In one aspect, a fecal microbe preparation described herein comprises a purified or reconstituted fecal bacterial mixture. In one aspect, a fecal microbe preparation described herein comprises a fecal microbiota preparation. In one aspect, a fecal microbe preparation comprises one or more, one or more, two or more, three or more, four or more, or five or more live fecal microorganisms are selected from the group consisting of *Acidaminococcus, Akkermansia, Alistipes, Anaerotruncus, Bacteroides, Bifidobacterium, Blautia, Butyrivibrio, Clostridium, Collinsella, Coprococcus, Corynebacterium, Dorea, Enterococcus, Escherichia, Eubacterium, Faecalibacterium, Haemophilus, Holdemania, Lactobacillus, Moraxella, Parabacteroides, Prevotella, Propionibacterium, Raoultella, Roseburia, Ruminococcus, Staphylococcus, Streptococcus, Subdoligranulum*, and *Veillonella*. In one aspect, a fecal microbe preparation comprises one or more, one or more, two or more, three or more, four or more, or five or more live fecal microorganisms are selected from the group consisting of *Bacteroides fragilis* ssp. *vulgatus, Collinsella aerofaciens, Bacteroides fragilis* ssp. *thetaiotaomicron, Peptostreptococcus productus* II, *Parabacteroides distasonis, Faecalibacterium prausnitzii, Coprococcus eutactus, Peptostreptococcus productus, Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. *A, Eubacterium biforme, Bifidobacterium infantis, Eubacterium rectale, Coprococcus comes, Pseudoflavonifractor capillosus, Ruminococcus albus, Dorea formicigenerans, Eubacterium hallii, Eubacterium ventriosum, Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Coprococcus catus, Aerostipes hadrus, Eubacterium cylindroides, Eubacterium ruminantium, Staphylococcus epidermidis, Eubacterium limosum, Tissirella praeacuta, Fusobacterium mortiferum, Fusobacterium naviforme, Clostridium innocuum, Clostridium ramosum, Propionibacterium acnes, Ruminococcus flavefaciens, Bacteroides fragilis* ssp. *ovatus, Fusobacterium nucleatum, Fusobacterium mortiferum, Escherichia coli, Gemella morbillorum, Finegoldia magnus, Streptococcus intermedius, Ruminococcus lactaris, Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus*, and *Desuifomonas pigra*.

In one aspect, a fecal microbe preparation lacks or is substantially devoid of one or more, one or more, two or more, three or more, four or more, or five or more live fecal microorganisms are selected from the group consisting of *Acidaminococcus, Akkermansia, Alistipes, Anaerotruncus, Bacteroides, Bifidobacterium, Blautia, Butyrivibrio, Clostridium, Collinsella, Coprococcus, Corynebacterium, Dorea, Enterococcus, Escherichia, Eubacterium, Faecalibacterium, Haemophilus, Holdemania, Lactobacillus, Moraxella, Parabacteroides, Prevotella, Propionibacterium, Raoultella, Roseburia, Ruminococcus, Staphylococcus, Streptococcus, Subdoligranulum*, and *Veillonella*. In one aspect, a fecal microbe preparation lacks or is substantially devoid of one or more, one or more, two or more, three or more, four or more, or five or live more fecal microorganisms are selected from the group consisting of *Bacteroides fragilis* ssp. *vulgatus*, *Collinsella aerofaciens*, *Bacteroides fragilis* ssp. *thetaiotaomicron*, *Peptostreptococcus productus* II, *Parabacteroides distasonis*, *Faecalibacterium prausnitzii*, *Coprococcus eutactus*, *Peptostreptococcus productus*, *Ruminococcus bromii*, *Bifidobacterium adolescentis*, *Gemmiger formicilis*, *Bifidobacterium longum*, *Eubacterium siraeum*, *Ruminococcus torques*, *Eubacterium rectale*, *Eubacterium eligens*, *Bacteroides eggerthii*, *Clostridium leptum*, *Bacteroides fragilis* ssp. *A*, *Eubacterium biforme*, *Bifidobacterium infantis*, *Eubacterium rectale*, *Coprococcus comes*, *Pseudoflavonifractor capillosus*, *Ruminococcus albus*, *Dorea formicigenerans*, *Eubacterium hallii*, *Eubacterium ventriosum*, *Fusobacterium russi*, *Ruminococcus obeum*, *Eubacterium rectale*, *Clostridium ramosum*, *Lactobacillus leichmannii*, *Ruminococcus callidus*, *Butyrivibrio crossotus*, *Acidaminococcus fermentans*, *Eubacterium ventriosum*, *Bacteroides fragilis* ssp. *fragilis*, *Coprococcus catus*, *Aerostipes hadrus*, *Eubacterium cylindroides*, *Eubacterium ruminantium*, *Staphylococcus epidermidis*, *Eubacterium limosum*, *Tissirella praeacuta*, *Fusobacterium mortiferum*, *Fusobacterium naviforme*, *Clostridium innocuum*, *Clostridium ramosum*, *Propionibacterium acnes*, *Ruminococcus flavefaciens*, *Bacteroides fragilis* ssp. *ovatus*, *Fusobacterium nucleatum*, *Fusobacterium mortiferum*, *Escherichia coli*, *Gemella morbillorum*, *Finegoldia magnus*, *Streptococcus intermedius*, *Ruminococcus lactaris*, *Eubacterium tenue*, *Eubacterium ramulus*, *Bacteroides clostridiiformis* ssp. *clostridliformis*, *Bacteroides coagulans*, *Prevotella oralis*, *Prevotella ruminicola*, *Odoribacter splanchnicus*, and *Desuifomonas pigra*.

In some aspects, a method of the present disclosure further comprises allowing the subject to intake only water for up to two hours prior to orally administrating a single dose of the pharmaceutical composition. In certain aspects, a method of the present disclosure comprises allowing the subject to intake only water for up to about half an hour, up to about one hour, up to about one and a half hour, or up to about two hours prior to orally administrating a single dose of the pharmaceutical composition. In an aspect, the method of the present disclosure further comprises allowing the subject to intake only water for up to two hours after orally administrating a single dose of the pharmaceutical composition. In certain aspects, a method of the present disclosure comprises allowing the subject to intake only water for up to about half an hour, up to about one hour, up to about one and a half hour, or up to about two hours after orally administrating a single dose of the pharmaceutical composition. In some aspects, the method of the present disclosure requires no colon purgative prior to the oral administering step. In certain aspects, the method of the present disclosure further comprises keeping the subject in an upright position for at least two hours after orally administrating a single dose of the pharmaceutical composition.

In some aspects, a method of the present disclosure further comprises storing the pharmaceutical composition at 4° C. or higher prior to the oral administering step. In an aspect, the method of the present disclosure further comprises storing the pharmaceutical composition at room temperature for at least 3 days prior to the oral administering step.

In an aspect, the pharmaceutical composition used in methods of the present disclosure comprising a freeze-dried fecal microbe preparation may comprise a cryoprotectant selected from the group consisting of trehalose, glucose, fructose, sucrose, lactose, ribose, mannitol, erythritol, arabitol, sorbitol, alanine, glycine, proline, sand a combination thereof.

In some aspects, the pharmaceutical composition used in methods of the present disclosure may be formulated as an enteric coated capsule or microcapsule, an acid-resistant capsule, an acid-resistant microcapsule, an enteric coated tablet, an acid-resistant tablet, an enteric coated geltab, an acid-resistant geltab, an enteric coated pill, or an acid-resistant pill. In certain aspects, the pharmaceutical composition of the present disclosure may be administered together with a food, a liquid beverage, a food additive, a dairy-based product, a soy-based product or a derivative thereof, a jelly, or a yogurt.

In some aspects, a single dose in accordance with the present disclosure comprises a total cell count of $10^{10}$ or lower, such as between about $10^3$ and about $10^{10}$, between about $10^4$ and about $10^{10}$, between about $10^5$ and about $10^{10}$, between about $10^6$ and about $10^{10}$, between about $10^7$ and about $10^9$, or between about $10^7$ and about $10^8$. In certain aspects, a single dose in accordance with the present disclosure comprises a total live cell count of $10^{10}$ or lower, such as between about $10^3$ and about $10^{10}$, between about $10^4$ and about $10^{10}$, between about $10^5$ and about $10^{10}$, between about $10^6$ and about $10^{10}$, between about $10^7$ and about $10^9$, or between about $10^7$ and about $10^8$.

In one aspect, a single dose in accordance with the present disclosure comprises at least about $10^5$, $10^6$, $10^7$, $10^8$, $10^9$, $10^{10}$, $10^{11}$, $10^{12}$, or $10^{13}$ cfu. In another aspect, a single dose comprises at most about $10^5$, $10^6$, $10^7$, $10^8$, $10^9$, $10^{10}$, $10^{11}$, $10^{12}$, or $10^{13}$ cfu. In a further aspect, a single dose is selected from the group consisting of from $10^8$ cfu to $10^{14}$ cfu, from $10^9$ cfu to $10^{13}$ cfu, from $10^{10}$ cfu to $10^{12}$ cfu, from $10^9$ cfu to $10^{14}$ cfu, from $10^9$ cfu to $10^{12}$ cfu, from $10^9$ cfu to $10^{11}$ cfu, from $10^9$ cfu to $10^{10}$ cfu, from $10^{10}$ cfu to $10^{14}$ cfu, from $10^{10}$ cfu to $10^{13}$ cfu, from $10^{11}$ cfu to $10^{14}$ cfu, from $10^{11}$ cfu to $10^{13}$ cfu, from $10^{12}$ cfu to $10^{14}$ cfu, and from $10^{13}$ cfu to $10^{14}$ cfu. In one aspect, a pharmaceutical composition comprises the foregoing single dose in a unit weight of about 0.2, 0.4, 0.6, 0.8 or 1.0 gram, or a unit volume of about 0.2, 0.4, 0.6, 0.8 or 1.0 milliliter.

In one aspect, a single dose in accordance with the present disclosure comprises at least about $10^5$, $10^6$, $10^7$, $10^8$, $10^9$, $10^{10}$, $10^{11}$, $10^{12}$, or $10^{13}$ cells or spores. In another aspect, a single dose comprises at most about $10^5$, $10^6$, $10^7$, $10^8$, $10^9$, $10^{10}$, $10^{11}$, $10^{12}$, or $10^{13}$ total cells or spores. In a further aspect, a single dose is selected from the group consisting of from $10^8$ to $10^{14}$, from $10^9$ to $10^{13}$, from $10^{10}$ to $10^{12}$, from $10^9$ to $10^{14}$, from $10^9$ to $10^{12}$, from $10^9$ to $10^{11}$, from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cells or spores. In an aspect, the single dose cell count is directed to live cells. In one aspect, a pharmaceutical composition comprises the foregoing single dose in a unit weight of about 0.2, 0.4, 0.6, 0.8 or 1.0 gram, or a unit volume of about 0.2, 0.4, 0.6, 0.8 or 1.0 milliliter.

In some aspects, a single dose of pharmaceutical composition of the present disclosure in accordance with the present disclosure is administered to a subject who had no prior exposure to fecal microbiota-based therapy. In certain aspects, a single dose of pharmaceutical composition in accordance with the current disclosure may eliminate or reduce gastrointestinal dysbiosis. In an aspect, a single dose of pharmaceutical composition in accordance with the current disclosure may increase bacterial diversity in a subject's gastrointestinal tract.

In certain aspects, within 3 to 6 days from orally administering a single dose of the pharmaceutical composition of the present application to a subject in need thereof, the relative abundance of *Proteobacteria* in the subject's stool may decrease by at least 30%. In certain aspects, the relative abundance of *Proteobacteria* in the subject's stool may decrease by at least 30% within 3 to 5 days, within 3 to 4 days, or within 4 to 5 days from orally administering a single dose of the pharmaceutical composition of the present application. In some aspects, the relative abundance of *Proteobacteria* in the subject's stool may decrease by at least 40%, at least 50%, at least 60%, at least 70%, at least 80%, at least 90%, at least 95%, or at least 98%, within 3 to 6 days from orally administering a single dose of the pharmaceutical composition of the present application.

In an aspect, within 3 to 6 days from orally administering a single dose of the pharmaceutical composition of the present application to a subject in need thereof, the relative abundance of *Firmicutes* in the subject's stool may increase by at least 30%. In certain aspects, the relative abundance of *Firmicutes* in the subject's stool may increase by at least 30% within 3 to 5 days, within 3 to 4 days, or within 4 to 5 days from orally administering a single dose of the pharmaceutical composition of the present application. In some aspects, the relative abundance of *Firmicutes* in the subject's stool may increase by at least 40%, at least 50%, at least 60%, at least 70%, at least 80%, at least 90%, at least 95%, or at least 98%, within 3 to 6 days from orally administering a single dose of the pharmaceutical composition of the present application.

In an aspect, within 3 to 6 days from orally administering a single dose of the pharmaceutical composition of the present application to a subject in need thereof, the relative abundance of *Bacteroidetes* in the subject's stool may increase by at least 30%. In certain aspects, the relative abundance of *Bacteroidetes* in the subject's stool may increase by at least 30% within 3 to 5 days, within 3 to 4 days, or within 4 to 5 days from orally administering a single dose of the pharmaceutical composition of the present application. In some aspects, the relative abundance of *Bacteroidetes* in the subject's stool may increase by at least 40%, at least 50%, at least 60%, at least 70%, at least 80%, at least 90%, at least 95%, or at least 98%, within 3 to 6 days from orally administering a single dose of the pharmaceutical composition of the present application.

In an aspect, within 3 to 6 days from orally administering a single dose of the pharmaceutical composition of the present application to a subject in need thereof, the alpha diversity of *Firmicutes* in the subject's stool may increase by at least 20%. In certain aspects, the alpha diversity of *Firmicutes* in the subject's stool may increase by at least 20% within 3 to 5 days, within 3 to 4 days, or within 4 to 5 days from orally administering a single dose of the pharmaceutical composition of the present application. In some aspects, the alpha diversity of *Firmicutes* in the subject's stool may increase by at least 25%, at least 30%, at least 35%, at least 40%, at least 45%, at least 50%, at least 55%, at least 60%, at least 70%, at least 80%, at least 90%, at least 100%, at least 150%, or at least 200%, within 3 to 6 days from orally administering a single dose of the pharmaceutical composition of the present application.

In an aspect, within 6 days from orally administering a single dose of the pharmaceutical composition of the present application to a subject in need thereof, the alpha diversity within *Bacteroidetes* in the subject's stool remains substantially unchanged. In some aspects, the alpha diversity within *Bacteroidetes* in the subject's stool remains substantially unchanged within 21 days or 60 days from orally administering a single dose of the pharmaceutical composition of the present application. In certain aspects, the alpha diversity within *Bacteroidetes* in the subject's stool exhibits a change of less than 20%, such as less than 15%, less than 10%, less than 8%, less than 6%, or less than 4% within 6 days from orally administering a single dose of the pharmaceutical composition of the present application. In an aspect, the alpha diversity within *Bacteroidetes* in the subject's stool exhibits a change of less than 20%, such as less than 15%, less than 10%, less than 8%, less than 6%, or less than 4% within 21 days from orally administering a single dose of the pharmaceutical composition of the present application. In another aspect, the alpha diversity within *Bacteroidetes* in the subject's stool exhibits a change of less than 20%, such as less than 15%, less than 10%, less than 8%, less than 6%, or less than 4% within 60 days from orally administering a single dose of the pharmaceutical composition of the present application.

In some aspects, a method in accordance with the present disclosure may eliminate or reduces one or more, two or more, three or more, four or more symptoms selected from the group consisting of diarrhoea, weight loss, bleeding, loss of appetite, abdominal pain, fever, and fatigue. In an aspect, such elimination or reduction of symptom occurs within at least 3 days, at least 1 week, at least 2 weeks, at least 3 weeks, at least 4 weeks, at least 5 weeks, at least 6 weeks from orally administering a single dose of the pharmaceutical composition of the present application.

In certain aspects, a method in accordance with the present disclosure further comprises providing a maintenance dosing schedule following the oral administration of a single dose. In some aspects, a maintenance dosing schedule comprises a dose lower or equal to the dose of the single dose. In an aspect, a maintenance dosing schedule lasts for a duration of at least about 2 months, at least about 4 months, at least about 6 months, at least about 8 months, at least about 10 months, at least about 12 months, at least about 18 months, at least about 24 months, at least about 36 months, at least about 48 months, at least about 72 months, or at least about 96 months. In certain aspects, there may be an interval of at least 1 week between the single dose oral administration and a maintenance dosing schedule. In some aspects, the interval may be at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks. In certain aspects, the maintenance dosing schedule is a continuous dosing schedule. In an aspect, the maintenance dosing schedule is an intermittent dosing schedule. In some aspects, an intermittent dosing schedule comprises a treatment period of at least 1 days, at least 2 days, at least 3 days, at least 4 days, at least 5 days, at least 6 days, at least 7 days, at least 8 days, at least 9 days, at least 10 days, at least 11 days, at least 12 days, at least 13 days, or at least 14 days followed by a resting period of at least 1 days, at least 2 days, at least 3 days, at least 4 days, at least 5 days, at least 6 days, at least 7 days, at least 8 days, at least 9 days, at least 10 days, at least 11 days, at least 12 days, at least 13 days, or at least 14 days.

In certain aspects, a method in accordance with the present disclosure further comprises pretreating the subject with an antibiotic prior to oral administration of a single dose of the pharmaceutical composition of the present disclosure. In some aspects, an antibiotic may be selected from the group consisting of amoxicillin, tetracycline, metronidazole, rifabutin, clarithromycin, clofazimine, vancomycin, rifampicin, nitroimidazole, chloramphenicol, and a combination thereof. In certain aspects, an antibiotic may be selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof.

In certain aspects, a method in accordance with the present disclosure further comprises pretreating the subject with an anti-inflammatory drug prior to oral administration of a single dose of the pharmaceutical composition of the present disclosure.

In some aspects, a fecal microbe preparation of the present disclosure may comprise a donor's entire or substantially complete microbiota. In certain aspects, a fecal microbe preparation of the present disclosure may comprise a non-selected fecal microbe. In some aspects, a fecal microbe preparation may comprise an isolated or purified population of live non-pathogenic fecal bacteria from cultures. In certain aspects, a fecal microbe preparation is substantially free of non-living matter. In some aspects, a fecal microbe preparation is substantially free of acellular material selected from the group consisting of residual fiber, DNA, viral coat material, and non-viable material. In an aspect, a fecal microbe preparation of the present disclosure may be substantially free of eukaryotic cells from the donor of the fecal microbe. In some aspects, a fecal microbiota preparation of the present disclosure comprises no antibiotic resistant population.

In certain aspects, a fecal microbe preparation of the present disclosure is prepared by a process comprising a treatment selected from the group consisting of ethanol treatment, detergent treatment, heat treatment, irradiation, and sonication, or a combination thereof. In some aspects, a fecal microbe preparation of the present disclosure is prepared by a process not requiring one or more treatments selected from the group consisting of ethanol treatment, detergent treatment, heat treatment, irradiation, and sonication. In an aspect, a fecal microbe preparation of the present disclosure is prepared by a process without any one of the following treatments: ethanol treatment, detergent treatment, heat treatment, irradiation, and sonication. In one aspect, a fecal microbe preparation of the present disclosure is prepared by a process involving a separation step selected from the group consisting of filtering, sieving, density gradients, filtration, chromatography, and a combination thereof. In one aspect, a fecal microbe preparation of the present disclosure is prepared by a process not requiring one or more separation steps selected from the group consisting of filtering, sieving, density gradients, filtration, and chromatography.

In an aspect, a fecal microbe preparation of the present disclosure is prepared from reconstituted fecal material. In another aspect, a fecal microbe preparation of the present disclosure is prepared from synthetic fecal material.

In an aspect, a pharmaceutical composition provided or administered herein comprises a fecal microbiota comprising a Shannon Diversity Index of greater than or equal to 2.0, greater than or equal to 2.1, greater than or equal to 2.2, greater than or equal to 2.3, greater than or equal to 2.4, greater than or equal to 2.5, greater than or equal to 3.0, greater than or equal to 3.1, greater than or equal to 3.2, greater than or equal to 3.3, greater than or equal to 3.4, greater than or equal to 3.5, greater than or equal to 3.6, greater than or equal to 3.7, greater than or equal to 3.8, greater than or equal to 3.9, greater than or equal to 4.0, greater than or equal to 4.1, greater than or equal to 4.2, greater than or equal to 4.3, greater than or equal to 4.4, greater than or equal to 4.5, or greater than or equal to 5.0. In another aspect, a pharmaceutical composition comprises fecal microbiota comprising a Shannon Diversity Index of between 2.5 and 5.0, between 2.7 and 5.0, between 2.9 and 5.0, between 3.1 and 5.0, between 3.3 and 5.0, between 3.5 and 5.0, between 3.7 and 5.0, between 3.9 and 5.0, or between 4.1 and 5.0. In one aspect, a Shannon Diversity Index is calculated at the phylum level. In another aspect, a Shannon Diversity Index is calculated at the family level. In one aspect, a Shannon Diversity Index is calculated at the genus level. In another aspect, a Shannon Diversity Index is calculated at the species level. In a further aspect, a pharmaceutical composition comprises a preparation of flora in proportional content that resembles a normal healthy human fecal flora.

In a further aspect, a pharmaceutical composition comprises fecal bacteria from at least 1, 2, 3, 4, 5, 6, 7, 8, 9, or 10 different families. In an aspect, a pharmaceutical composition provided or administered herein comprises a fecal microbiota comprising no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. In another aspect, a pharmaceutical composition provided or administered herein comprises a fecal microbiota comprising no greater than 20%, 25%, 30%, 35%, 40%, 45%, 50%, 55%, 60%, 65%, 70%, 75%, 80%, 85%, 90%, or 95% weight non-living material/weight biological material. In another aspect, a pharmaceutical composition provided or administered herein comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In one embodiment, "biological material" refers to the living material, e.g., the microbes, eukaryotic cells, and viruses, which are present in the colon of a normal healthy human. In an aspect, a pharmaceutical composition provided or administered herein comprises an extract of human feces where the composition is substantially odorless. In an aspect, a pharmaceutical composition provided or administered herein comprises fecal material or a fecal floral preparation in a lyophilized, crude, semi-purified or purified formulation.

In an aspect, a fecal microbiota in a pharmaceutical composition comprises highly refined or purified fecal microflora, e.g., substantially free of non-floral fecal material. In an aspect, a fecal microbiota can be further processed, e.g., to undergo microfiltration before, after, or before and after sieving. In another aspect, a highly purified fecal microbiota product is ultra-filtrated to remove large molecules but retain the therapeutic microflora, e.g., bacteria.

In another aspect, a fecal microbiota in a pharmaceutical composition used herein comprises or consists essentially of a substantially isolated or a purified fecal flora or entire (or substantially entire) microbiota that is (or comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or, a substantially isolated, purified, or substantially entire microbiota as described in Sadowsky et al., WO 2012/122478 A1, or as described in Borody et al., WO 2012/016287 A2.

In an aspect, a fecal microbiota in a pharmaceutical composition comprises a donor's substantially entire or non-selective fecal microbiota, reconstituted fecal material, or synthetic fecal material. In another aspect, the fecal microbiota in a pharmaceutical composition comprises no antibiotic resistant population. In another aspect, a pharmaceutical composition comprises a fecal microbiota and is largely free of extraneous matter (e.g., non-living matter including acellular matter such as residual fiber, DNA, RNA, viral coat material, non-viable material; and living matter such as eukaryotic cells from the fecal matter's donor).

In an aspect, a fecal microbiota in a pharmaceutical composition used herein is derived from disease-screened fresh homologous feces or equivalent freeze-dried and reconstituted feces. In an aspect, a fresh homologous feces does not include an antibiotic resistant population. In another aspect, a fecal microbiota in a pharmaceutical composition is derived from a synthetic fecal composition. In an aspect, a synthetic fecal composition comprises a preparation of viable flora which preferably in proportional content, resembles normal healthy human fecal flora which does not include antibiotic resistant populations. Suitable microorganisms may be selected from the following: *Bacteroides, Eubacterium, Fusobacterium, Propionibacterium, Lactobacillus, Ruminococcus, Escherichia coli, Gemmiger, Clostridium, Desulfomonas, Peptostreptococcus, Bifidobacterium, Collinsella, Coprococcus, Dorea,* and *Ruminococcus*.

In an aspect, a pharmaceutical composition is combined with other adjuvants such as antacids to dampen bacterial inactivation in the stomach. (e.g., Mylanta, Mucaine, Gastrogel). In another aspect, acid secretion in the stomach could also be pharmacologically suppressed using $H_2$-antagonists or proton pump inhibitors. An example $H_2$-antagonist is ranitidine. An example proton pump inhibitor is omeprazole. In one aspect, an acid suppressant is administered prior to administering, or in co-administration with, a pharmaceutical composition.

In some aspects, a fecal microbe preparation of the present disclosure comprises a preparation of viable flora in proportional content that resembles a normal healthy human fecal flora. In certain aspects, a fecal microbe preparation of the present disclosure comprises bacteria from at least 2, at least 3, at least 4, at least 5, at least 6, at least 7, at least 8, at least 9, at least 10, at least 12, at least 15, at least 18, or at least 20 different families. In some aspects, a fecal microbe preparation of the present disclosure comprises bacteria from at least 2, at least 3, at least 4, at least 5, at least 6, at least 7, at least 8, at least 9, at least 10, at least 12, at least 15, at least 18, at least 20, at least 23, at least 25, at least 27, at least 30, at least 32, at least 35, at least 38, or at least 40 different genera. In certain aspects, a fecal microbe preparation of the present disclosure has a Shannon Diversity Index of 0.4-5.0 at the family, genus, or species level.

In some aspects, a fecal microbe preparation of the present disclosure has at least about 20%, at least about 30%, at least about 40%, at least about 50%, at least about 60%, at least about 70%, at least about 80%, at least about 85%, at least about 90%, at least about 95%, at least about 99%, or at least about 99.5% microbes in a spore form. In certain aspects, a fecal microbe preparation of the present disclosure has at least about 20%, at least about 30%, at least about 40%, at least about 50%, at least about 60%, at least about 70%, at least about 80%, at least about 85%, at least about 90%, at least about 95%, at least about 99%, or at least about 99.5% microbes in a non-spore form.

In an aspect, the present disclosure provides for the following exemplary embodiments:

Embodiment 1: A method for treating a *Clostridium difficile* infection (CDI) in a subject in need thereof, said method comprising orally administering to said subject a single dose of a pharmaceutical composition comprising a freeze-dried fecal microbiota preparation, wherein said single dose achieves a CDI clearance rate of at least 80%.

Embodiment 2: A method for treating a *Clostridium difficile* infection (CDI) in a subject in need thereof, said method comprising orally administering to said subject a single dose of a pharmaceutical composition comprising a freeze-dried fecal microbiota preparation, wherein said single dose is capable of achieving a CDI clearance rate of at least 80%.

Embodiment 3: The method of embodiment 1 or 2, wherein said CDI clearance rate is calculated based on a patient population size of 20, 30, 40, 50, or 100.

Embodiment 4: The method of embodiment 1 or 2, wherein the relative abundance of *Proteobacteria* in said subject's stool decreases by at least 50% within 3 to 6 days from administering said single dose relative to a baseline abundance immediately prior to administering said single dose.

Embodiment 5: The method of embodiment 1 or 2, wherein the relative abundance of *Firmicutes* in said subject's stool increases by at least 50% within 3 to 6 days from administering said single dose relative to a baseline abundance immediately prior to administering said single dose.

Embodiment 6: The method of embodiment 1 or 2, wherein the relative abundance of *Bacteroidetes* in said subject's stool increases by at least 50% within 3 to 6 days from administering said single dose relative to a baseline abundance immediately prior to administering said single dose.

Embodiment 7: The method of embodiment 1 or 2, wherein the alpha diversity within *Firmicutes* in said subject's stool increases by at least 100% within 3 to 6 days from administering said single dose relative to a baseline diversity immediately prior to administering said single dose.

Embodiment 8: The method of embodiment 1 or 2, wherein the alpha diversity within *Bacteroidetes* in said subject's stool remains substantially unchanged within 6 days, 21 days, or 60 days from administering said single dose relative to a baseline diversity immediately prior to administering said single dose.

Embodiment 9: The method of embodiment 1 or 2, wherein the alpha diversity within *Bacteroidetes* in said subject's stool exhibits a change of less than 15% within 6 days, 21 days, or 60 days from administering said single dose relative to a baseline diversity immediately prior to administering said single dose.

Embodiment 10: The method of embodiment 1 or 2, wherein said single dose achieves a CDI clearance rate of at least 85%, 88%, 90%, 92%, 94%, 96%, 98%, or 99%.

Embodiment 11: The method of embodiment 1 or 2, wherein said subject is allowed only water for two hours prior to said administering said pharmaceutical composition.

Embodiment 12: The method of embodiment 1 or 2, wherein said subject is allowed only water for two hours after said administering said pharmaceutical composition.

Embodiment 13: The method of embodiment 1 or 2, wherein said subject remains upright for at least two hours after said administering said pharmaceutical composition.

Embodiment 14: The method of embodiment 1 or 2, wherein said subject experience little or no bowel movement irregularity, bloating, or flatulence within the first two weeks from administering said single dose.

Embodiment 15: The method of embodiment 1 or 2, wherein said pharmaceutical composition is stored at 4° C. or higher prior to said administering.

Embodiment 16: The method of embodiment 1 or 2, wherein said pharmaceutical composition is stored at 4° C. or lower prior to said administering.

Embodiment 17: The method of embodiment 1 or 2, wherein said pharmaceutical composition is stored at −20° C. or −80° C. for long term storage.

Embodiment 18: The method of embodiment 1 or 2, wherein said pharmaceutical composition is capable being stored at room temperature for at least 3 days prior to said administering.

Embodiment 19: The method of embodiment 1 or 2, wherein said method requires no colon purgative prior to administering said single dose.

Embodiment 20: The method of embodiment 1 or 2, wherein said pharmaceutical composition is formulated as an enteric coated capsule or microcapsule, an acid-resistant capsule or microcapsule, an enteric coated tablet, an acid-resistant tablet, an enteric coated geltab, an acid-resistant geltab, an enteric coated pill, or an acid-resistant pill.

Embodiment 21: The method of embodiment 1 or 2, wherein said pharmaceutical composition is administered together with a food, a liquid beverage, a food additive, a dairy-based product, a soy-based product or a derivative thereof, a jelly, or a yogurt.

Embodiment 22: The method of embodiment 1 or 2, wherein said single dose comprises a total cell count of $10^{10}$ or greater.

Embodiment 23: The method of embodiment 1 or 2, wherein said single dose comprises a total cell count of $10^{10}$ or lower.

Embodiment 24: The method of embodiment 1 or 2, wherein said single dose comprises a total live cell count of $10^{10}$ or lower.

Embodiment 25: The method of embodiment 22, wherein said single dose comprises a total cell count or a total live cell count between about $10^3$ and about $10^{10}$, between about $10^4$ and about $10^{10}$, between about $10^5$ and about $10^{10}$, between about $10^6$ and about $10^{10}$, between about $10^7$ and about $10^9$, or between about $10^7$ and about $10^8$.

Embodiment 26: The method of embodiment 1 or 2, wherein said freeze-dried fecal microbiota preparation comprises a cryoprotectant selected from the group consisting of trehalose, glucose, fructose, sucrose, lactose, ribose, mannitol, erythritol, arabitol, sorbitol, alanine, glycine, proline, sand a combination thereof.

Embodiment 27: The method of embodiment 1 or 2, wherein said CDI is primary CDI.

Embodiment 28: The method of embodiment 1 or 2, wherein said CDI is recurrent CDI.

Embodiment 29: The method of embodiment 1 or 2, wherein said single dose is said subject's first ever fecal microbiota-based therapy.

Embodiment 30: The method of embodiment 1 or 2, wherein said fecal microbiota preparation comprises a donor's entire or substantially complete microbiota.

Embodiment 31: The method of embodiment 1 or 2, wherein said fecal microbiota preparation comprises a non-selected fecal microbiota.

Embodiment 32: The method of embodiment 1 or 2, wherein said fecal microbiota preparation comprises an isolated or purified population of live non-pathogenic fecal bacteria from culturing.

Embodiment 33: The method of embodiment 1 or 2, wherein the preparation of said fecal microbiota preparation involves a treatment selected from the group consisting of ethanol treatment, detergent treatment, heat treatment, irradiation, and sonication, and a combination thereof.

Embodiment 34: The method of embodiment 1 or 2, wherein the preparation of said fecal microbiota preparation involves no treatment selected from the group consisting of ethanol treatment, detergent treatment, heat treatment, irradiation, and sonication.

Embodiment 35: The method of embodiment 1 or 2, wherein the preparation of said fecal microbiota preparation involves a separation step selected from the group consisting of filtering, sieving, differential centrifugation, density gradient centrifugation, filtration, chromatography, and a combination thereof.

Embodiment 36: The method of embodiment 1 or 2, wherein the preparation of said fecal microbiota preparation does not require one or more separation steps selected from the group consisting of filtering, sieving, density gradients, filtration, and chromatography.

Embodiment 37: The method of embodiment 1 or 2, wherein said fecal microbiota preparation is substantially free of non-living matter.

Embodiment 38: The method of embodiment 1 or 2, wherein said fecal microbiota preparation is substantially free of acellular material selected from the group consisting of residual fiber, DNA, viral coat material, and non-viable material.

Embodiment 39: The method of embodiment 1 or 2, wherein said fecal microbiota preparation is substantially free of eukaryotic cells from said fecal microbe's donor.

Embodiment 40: The method of embodiment 1 or 2, wherein said fecal microbiota preparation is from reconstituted fecal material.

Embodiment 41: The method of embodiment 1 or 2, wherein said fecal microbiota preparation is from synthetic fecal material.

Embodiment 42: The method of embodiment 1 or 2, wherein said fecal microbiota preparation comprises no antibiotic resistant population.

Embodiment 43: The method of embodiment 1 or 2, wherein said fecal microbiota preparation comprises a preparation of viable flora in proportional content that resembles a normal healthy human fecal flora.

Embodiment 44: The method of embodiment 1 or 2, wherein said fecal microbiota preparation comprises bacteria from at least 2, 3, 4, 5, 6, 7, 8, 9, 10, 12, 15, 18, or 20 different families.

Embodiment 45: The method of embodiment 1 or 2, wherein said fecal microbiota preparation comprises bacteria from at least 2, 3, 4, 5, 6, 7, 8, 9, 10, 12, 15, 18, 20, 23, 25, 27, 30, 32, 35, 38, or 40 different genera.

Embodiment 46: The method of embodiment 1 or 2, wherein said fecal microbiota preparation has a Shannon Diversity Index between 3.0 and 4.5 at the species level.

Embodiment 47: The method of embodiment 1 or 2, wherein said fecal microbiota preparation has at least about 20%, 30%, 40%, 50%, 60%, 70%, 80%, 85%, 90%, 95%, 99%, or 99.5% microbes in a spore form.

Embodiment 48: The method of embodiment 1 or 2, wherein said fecal microbiota preparation has at least about 20%, 30%, 40%, 50%, 60%, 70%, 80%, 85%, 90%, 95%, 99%, or 99.5% microbes in a non-spore form.

Embodiment 49: The method of embodiment 1 or 2, wherein said single dose is followed by a maintenance dosing schedule.

Embodiment 50: The method of embodiment 49, wherein said maintenance dosing schedule comprises a dose lower or equal to the dose of said single dose.

Embodiment 51: The method of embodiment 49, wherein said second dosing schedule lasts for at least about 2, 4, 6, 8, 10, 12, 18, 24, 36, 48, 72, or 96 months.

Embodiment 52: The method of embodiment 49, wherein the interval between said single dose and said maintenance dosing schedule is at least about 1, 2, 3, 4, 5, 6, 7, 8, 9, 10, 11, or 12 weeks.

Embodiment 53: The method of embodiment 49, wherein said maintenance dosing schedule is a continuous dosing schedule.

Embodiment 54: The method of embodiment 49, wherein said maintenance dosing schedule is an intermittent dosing schedule.

Embodiment 55: The method of embodiment 54, wherein said intermittent dosing schedule comprises a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days.

Embodiment 56: The method of any one of preceding embodiments, wherein said single dose eliminates or reduces gastrointestinal dysbiosis.

Embodiment 57: The method of any one of preceding embodiments, wherein said single dose increases bacterial diversity in said subject's gastrointestinal tract.

Embodiment 58: The method of any one of preceding embodiments, wherein said subject is pretreated with an antibiotic prior to administration of said composition.

Embodiment 59: The method of embodiment 58, wherein said antibiotic is selected from the group consisting of amoxicillin, tetracycline, metronidazole, rifabutin, clarithromycin, clofazimine, vancomycin, rifampicin, nitroimidazole, chloramphenicol, and a combination thereof.

Embodiment 60: The method of embodiment 58, wherein said antibiotic is selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof.

Embodiment 61: The method of any one of preceding embodiments, wherein said subject is pretreated with an anti-inflammatory drug prior to administration of said composition.

Embodiment 62: The method of any one of preceding embodiments, wherein said method eliminates or reduces one or more, two or more, three or more, four or more symptoms selected from the group consisting of diarrhea, weight loss, bleeding, loss of appetite, abdominal pain, fever, and fatigue.

While the present disclosure has been described with reference to preferred embodiments, it will be understood by those skilled in the art that various changes may be made and equivalents may be substituted for elements thereof to adapt to particular situations without departing from the scope of the present disclosure. Therefore, it is intended that the present disclosure not be limited to the particular embodiments disclosed as the best mode contemplated for carrying out the present disclosure, but that the present disclosure will include all embodiments falling within the scope and spirit of the appended claims.

EXAMPLES

Example 1

Fecal bacteria are prepared using the standard methods as previously described in Hamilton et al. Am. J. Gastroenterology 2012; 107:761-7, except that glycerol is substituted with one of the following cryoprotectants (all chemicals were USP grade or better and prepared in PBS, pH 7.0): 5% sucrose only; 10% sucrose only; 10% skim milk only; 5% trehalose only; 10% trehalose only; 10% trehalose plus 2.5% sucrose; 5% trehalose plus 2.5% sucrose; 5% mannitol only; or 10% mannitol only. The lyophilizer (LyoStar II, Stone Ridge, N.Y., or equivalent) used has a shelf temperature of −20° C. for 36 hours followed by 6 hours at +30° C. All steps are done under 100 mT vacuum or less, and the final product is held at +20° C. until used. The total dose is $2.5 \times 10^{12}$ cells.

Specifically, the cyroprotectants mannitol and trehalose, at 5% or 10% concentrations yield preparations that can be broken into a fine powder and easily packaged into capsules. However, viability of bacteria with trehalose is superior compared to mannitol, as measured by their membrane integrity (Table 1) and nearly indistinguishable (~4% loss of viability) compared to fresh fecal microbiota. In particular, membrane integrity is stable for up to 8 weeks post-lyophilization. Additionally, there is little difference in viability between preparations made with 5% trehalose compared to 10% trehalose, with lesser amount of trehalose allowing dosing in fewer capsules. Consequently, trehalose is chosen as the standard cryoprotrectant in all further studies.

TABLE 1

Percent intact cell viability data from frozen (liquid) and lyophilized material obtained from a single sample at various timepoints after processing/lyophilization.

| Material | Raw material - 60.2% intact Time (weeks) | | | | | | |
|---|---|---|---|---|---|---|---|
| | after 1 yo | 1 | 2 | 3 | 4 | 6 | 8 |
| Frozen - 10% glycerol | N/A | 55.1 | 58.1 | 53.4 | 57.2 | 56.2 | 55.3 |
| 10% Mannitol | 31.7 | 34.4 | 33.4 | 32.2 | 36.3 | 29.2 | 34.2 |
| 5% Mannitol | 29.5 | 32.1 | 27.6 | 30.1 | 28.6 | 31.3 | 28.4 |
| 10% Trehalose | 56.7 | 57.4 | 55.3 | 55.6 | 53.1 | 56.4 | 52.1 |
| 5% Trehalose | 59.4 | 55.4 | 58.9 | 57.2 | 56.2 | 52.2 | 55.8 |

Membrane integrity of freeze-dried microbiota remains intact after 96 hours of storage at room temperature, 4° C.

and −20° C. (Table 2). Cell counts and membrane integrity are determined from triplicate samples of fresh microbiota prepared following filtration steps and holding at room temperature, 4° C., and −20° C. for 96 hours. Results of this experiment show that there is no significant difference in cell integrity in samples held at room temperature, 4° C., or −20° C., relative to that found in the initial preparation.

TABLE 2

Temperature stability of encapsulated freeze-dried microbiota.

|  |  | Counts/square |  |  |  |  |  |  | Membrane |
|---|---|---|---|---|---|---|---|---|---|
|  |  | 1 | 2 | 3 | 4 | 5 | Average | Cells/g | Integrity |
| Sample 1 | Initial | 69 | 67 | 64 | 57 | 58 | 63 | 7.9E+11 | 49% |
|  | −20° C. | 56 | 52 | 50 | 49 | 48 | 51 | 6.4E+11 | 51% |
|  | +4° C. | 40 | 44 | 49 | 52 | 37 | 44 | 5.6E+11 | 58% |
|  | Room Temperature | 66 | 56 | 57 | 55 | 49 | 57 | 7.1E+11 | 54% |
| Sample 2 | Initial | 57 | 55 | 53 | 60 | 57 | 56 | 7.1E+11 | 61% |
|  | −20° C. | 57 | 68 | 60 | 56 | 60 | 60 | 7.5E+11 | 63% |
|  | +4° C. | 55 | 64 | 50 | 49 | 58 | 55 | 6.9E+11 | 65% |
|  | Room Temperature | 67 | 62 | 74 | 56 | 55 | 63 | 7.9E+11 | 63% |
| Sample 3 | Initial | 89 | 83 | 85 | 82 | 83 | 84 | 1.1E+12 | 55% |
|  | −20° C. | 90 | 87 | 88 | 82 | 92 | 88 | 1.1E+12 | 68% |
|  | +4° C. | 72 | 68 | 73 | 66 | 70 | 70 | 8.7E+11 | 55% |
|  | Room Temperature | 95 | 78 | 81 | 91 | 83 | 86 | 1.1E+12 | 49% |

Example 2

Germ-free mice are bred and maintained in the germ free facility at the Mayo Clinic (Rochester, Minn., USA). Animals are administered microbiota or PBS via oral gavage, 100 μL per dose. Microbiota preparations include frozen/thawed liquid with 10% glycerol, as described previously or rehydrated freeze-dried microbiota in 5% trehalose. The dosage to each mouse, of either frozen or freeze-dried material, is $10^{10}$ cells. Fecal pellets are collected prior to gavage, as well as 3, 7, 14, and 21 days following gavage.

Figure 1B:
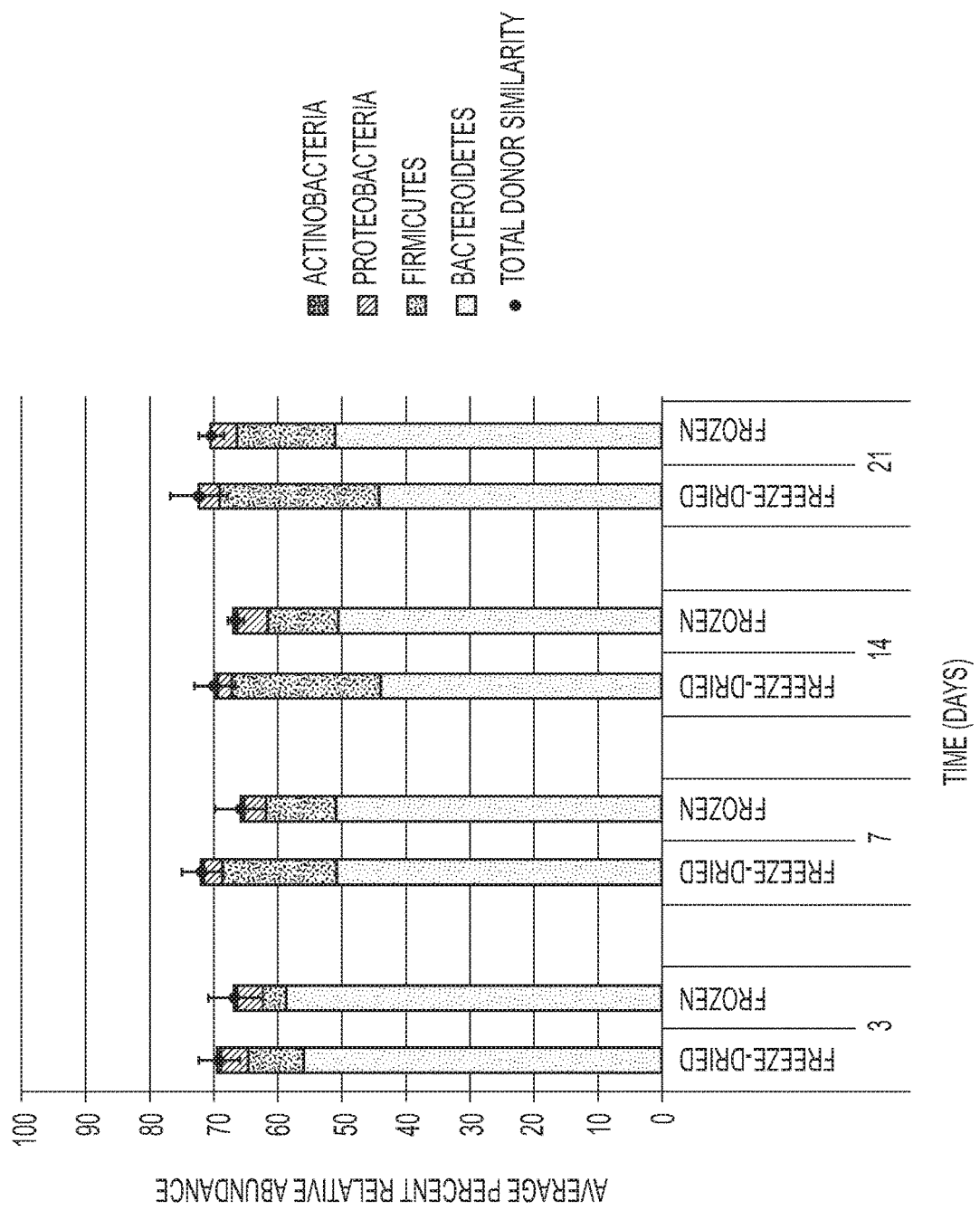
FIG. 1B shows the Phylum-level classification of OTUs that were associated with donor contribution in accordance with Example 2 of the present disclosure.

In order to ensure that the different taxa of microbiota are preserved by the freeze-drying protocol, preparations in germ free mice are tested. Comparison is made to frozen/thawed liquid preparation with glycerol. Prompt and stable engraftment of all bacterial phyla is evident for both frozen and freeze-dried treatment groups. FIG. 1A shows a distribution of phyla among all mouse fecal pellets and donor samples, without rarefication. FIG. 1B shows the Phylum-level classification of OTUs that are associated with donor contribution. Error bars reflect standard error of the mean.

Figure 2:
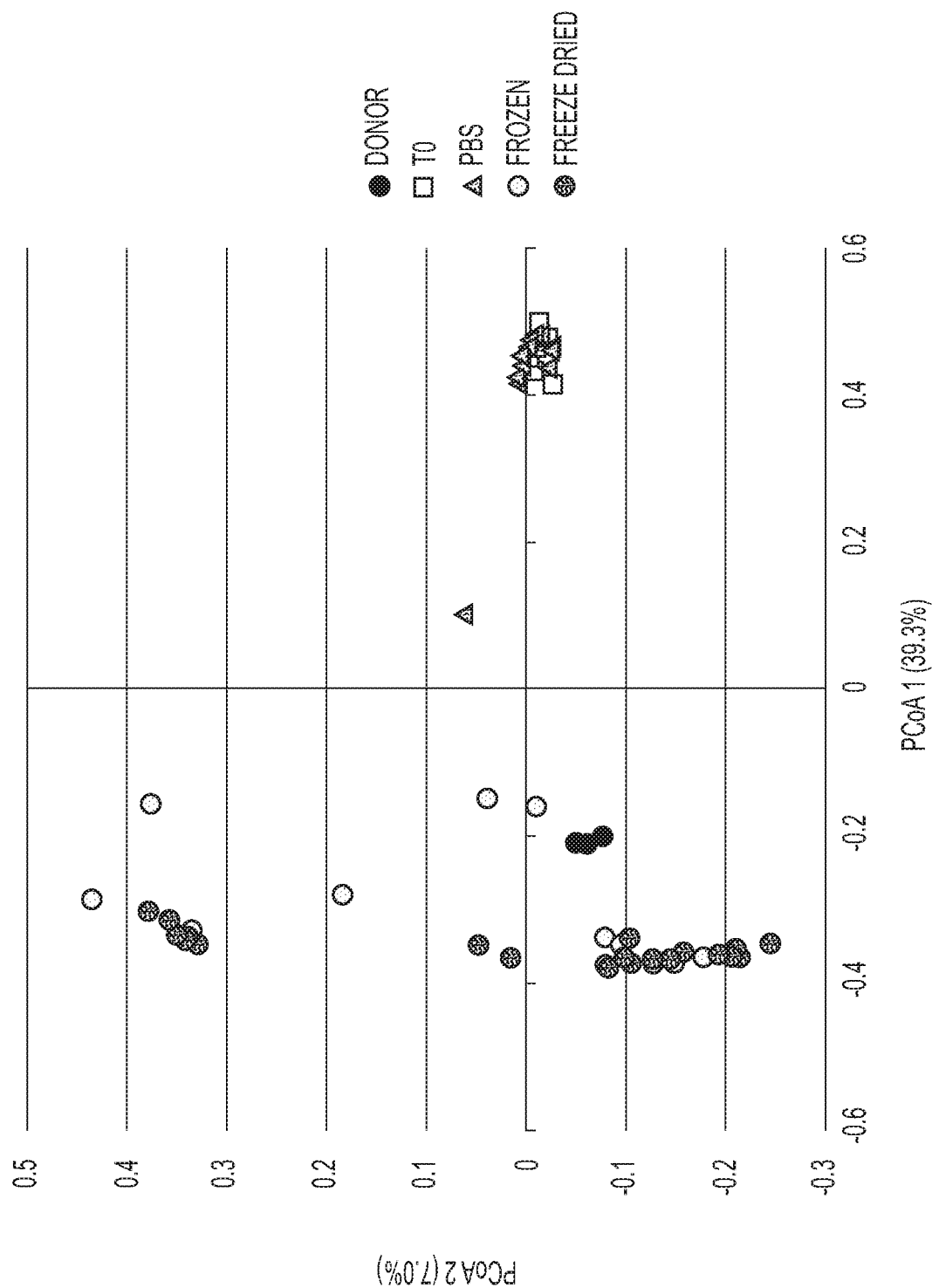
FIG. 2 shows a principal coordinate analysis of donor and germ-free mouse samples gavaged with PBS control, frozen, or freeze-dried fecal microbiota in accordance with Example 2 of the present disclosure.

Following gavage, engraftment proceeds as an early expansion of the *Bacteroidetes*, predominantly among the families Porphyromonadaceae and Bacteroidaceae, with a subsequent increase in the relative abundance of *Firmicutes*, primarily the families Lachnospiraceae and Ruminococcaceae (FIG. 1A). Engraftment is evident for both frozen and freeze-dried treatment groups at three days post-gavage ($T_3$; FIG. 1B), with donor OTUs accounting for >50% of the communities. The donor community appears to establish more quickly using the freeze-dried preparation, but differences between preparation are not significant at $T_3$ ($p=0.101$) or across all timepoints ($p=0.237$). Community composition of both frozen and freeze-dried treatment groups vary from each other as well as from donor communities by ANOSIM ($p<0.001$), and each group clusters independently (AMOVA $p<0.001$, FIG. 2).

Example 3

Double-encapsulated capsules are prepared by using a filled size 0 capsule packaged inside a size 00 capsule. Hypromellose capsules are DRcaps® from Capsugel (Morristown, N.J.). Capsules are manually filled using a 24-hole filler (Capsule Machine, Capsule Connection, Prescott, Ariz.) to a final concentration of $1 \times 10^{11}$ cells/capsule. The capsules are stored at −80° C. (a convenient dry storage option) in 50 mL conical tubes until needed. Once taken out of the freezer, a dessicant packet is added to the container. The length of storage period at −80° C. does not appear to impact the effectiveness of the capsules (Table 3).

TABLE 3

Storage duration of encapsulated microbiota prior to dispensing to the patients.

| Duration in −80° C. storage | Number of patients that underwent rescue capsule FMT following failure of colonoscopic FMT: failure/success | Patients that underwent their first FMT using capsule administration: failure/success |
|---|---|---|
| 0-3 months | 3/4 | 3/15 |
| 3-6 months | 1/0 | 0/5 |
| 6-9 months | 0/1 | 0/3 |
| 9-12 months | 1/0 | 1/12 |

Example 4

All patients offered initial FMT in the University of Minnesota program, from its inception in 2008 inclusive of the experience described here, satisfy formal inclusion and exclusion criteria, described previously in Khoruts et al. Clin. Gastroenterol. Hepatol. 2016. Briefly, these inclusion criteria are: (1) informed consent; (2) documentation of at least two spontaneous relapses of CDI following the initial episode of the infection; (3) failure of at least one extended antibiotic regimen (≥6 weeks) to clear the infection; (4) documentation of CDI by stool testing within three months of FMT. Exclusion criteria for all FMT patients include: (1) anticipation of non-CDI antibiotic treatment within three months of FMT; (2) life expectancy of less than two years if the patient is able to tolerate suppressive therapy with vancomycin, 125 mg daily, or rifaximin for patients with liver disease and hepatic encephalopathy. In addition, exclusion criteria for FMT with an encapsulated oral preparation of FMT in this study include: (1) dysphagia, (2) known inflammatory bowel disease (IBD), (3) absence of clinical indications for a diagnostic colonoscopy, (4) any immunosuppressive therapy or presence of known immune deficiency (e.g., IgA deficiency), (5) failure to obtain informed consent for capsule FMT. Patients excluded from capsule FMT are offered colonoscopic FMT as an option if the general inclusion/exclusion criteria are satisfied.

Some patients included in this cohort are recipients of previous FMT, administered via colonoscopy. In this program, patients suffering a spontaneous recurrence of CDI, i.e., relapse of the infection without a new antibiotic provocation, are offered another round of FMT. If the patients suffer a re-infection with CDI, i.e., relapse following a new antibiotic provocation, they are offered one round of anti-CDI antibiotic (preferably fidaxomicin, metronidazole, or vancomycin) and FMT only following a spontaneous relapse following such antibiotic treatment attempt.

Donor material used in preparation of FMT capsules is obtained from standard donors as previously described (University of Minnesota IRB donor protocol 1303M29782, Khoruts et al. Clin. Gastroenterol. Hepatol. 2016). Material for capsule FMT preparations is provided by two male donors. A medical personnel delivers the FMT capsules to patient homes and reinforces instructions for the FMT protocol. In the beginning, when patients are prepared with a colon purgative, vancomycin is continued until one day prior to FMT. Once the colon purgative is eliminated from the protocol, the patients discontinue vancomycin two days prior to FMT. The patients are told they could keep the capsules in the refrigerator for two days. The patients are allowed only water for two hours prior to taking the capsules. Only water is allowed for two hours after taking the capsules during which time the patients had to remain upright. The protocol evolves in the course of clinical experience as described further in the results section. Variables include (1) administration of a colon purgative prior to capsule FMT (discontinued after the first four patients; (2) acid suppressive medications; (3) the dose of FMT—this is decreased in the course of the study due to limited quantity of prepared material associated with reduction in key laboratory personnel.

In a single center (University of Minnesota) pragmatic study describing the entire clinical experience with capsule FMT from June 2014 to March 2016, failure of FMT is defined as spontaneous relapse of diarrheal symptoms and positive stool testing for *C. difficile* toxin B by PCR within two months of administration. *C. difficile* toxin B is measured in all patients that noted or complained of loose stools, regardless of frequency. All patients are seen in clinic after two months for a follow-up clinic visit following capsule FMT and are instructed to remain in contact with the clinic indefinitely with any new questions or concerns and any new prescriptions for antibiotics by other providers. The study is approved by the University of Minnesota Institutional Review Board.

The basic characteristics of the patients in this clinical cohort are comparable to patients without underlying IBD offered FMT in this program. These patients fail all reasonable attempts at breaking the cycle of R-CDI with antibiotics alone.

The clinical capsule FMT protocol evolves over the course of the program. The initial dose (~$2.5 \times 10^{12}$ bacteria, 24-27 capsules) is based on previous colonoscopic experience, which emerged from crude and arbitrary dosing based on stool weight. The capsules are administered over 2-3 days, 2-3 times per day on an empty stomach. The first four patients are instructed to take a colon purgative, identical to the one they would have received prior to colonoscopic FMT, before taking the capsules. The fifth patient is a paraplegic for whom taking the purgative presented an extreme difficulty. Therefore, she does not receive the purgative, but instead lengthened the period off vancomycin to two days prior to initiating the capsule FMT. The clinical outcome is successful, and based on this anecdotal evidence the purgative preparatory step is eliminated from the protocol for all other patients onwards.

The patients may not immediately embrace the capsule FMT protocol, despite its relative ease of administration. During the consent process, extensive experience with the colonoscopic FMT and relative novelty of the new capsule protocol are communicated to patients. Patients, exhausted with the cycles of CDI recurrence, prefer a treatment with known history of success. Therefore, the early patients electing the capsule are predominantly ones who suffered either spontaneous recurrence or antibiotic-triggered reinfection with *C. difficile* after being treated with colonoscopic FMT. These patients welcome the option without the colonoscopy, possibly because they feel discouraged and want to try something new. In fact, over the first six months of capsule FMT availability, four patients are treated with capsule FMT and 31 colonoscopic FMTs are performed. However, the pace of acceptance of the capsule FMT alternative gradually increases with the growth of clinical experience with this preparation and ability to inform the patients about the clinical outcomes.

Due to the limited supply of capsules, it is necessary to ration the doses. At first, the initial dose is halved and the next 14 patients receive $1.25 \times 10^{12}$ bacteria (14 capsules taken within one day). Finally, the original dose is decreased by an order of magnitude and the last 30 patients are dosed at $2.1-2.5 \times 10^{11}$ bacteria (2-4 capsules, single ingestion). The patients report no difficulty or esthetic concerns taking the capsules at any dose.

The success rate in clearing CDI is 83.8% (41/49 patients) in the entire cohort. The success rate among all patients for whom the capsule treatment is their first FMT is 89.7% (35/39 patients). One of these patients receives broad-spectrum antibiotics during a hospitalization for a complex urinary infection (the patient had urinary stents) within a day following her capsule FMT and suffers a re-infection with CDI. The success rate in clearing CDI for the lowest dosage of microbiota is 93.3% (28/30 patients) and 96.2% (25/26) for patients for whom the capsule treatment is their first FMT. Two patients out of the entire cohort suffer a spontaneous relapse of CDI after the 2-month end-point. No serious adverse events is observed in this cohort with the exception of the mentioned patient with the urinary infection. Approximately a third of patients report some bowel movement irregularity, bloating, and flatulence in the initial weeks following capsule FMT.

Example 5

Fecal samples are collected by patients into sterile containers within a week prior to FMT, on post-FMT days 3, 7, 14, and post-FMT months 1, 3, and 6-12. The samples are kept frozen until pick-up by the research assistant and are transported on ice into the laboratory.

A 250-500 mg amount of human fecal material is extracted using the PowerSoil® DNA Isolation Kit (MoBio Laboratories, Inc., Carlsbad, Calif., USA) without deviation from the manufacturer's instructions. The microbiome is characterized from patients for whom capsule FMT represented their first intervention (i.e. no prior colonoscopic FMT) and those that experienced any recurrence of infection, regardless of prior intervention. The V5+V6 hypervariable regions of the 16S rRNA gene are amplified at the University of Minnesota Genomics Center (UMGC, Minneapolis, Minn., USA) using the BSF784/1064R primer set. (Sogin et al. Proc. Natl. Acad. Sci. USA 2006; 103:12115-20; Claesson et al. Nucleic Acids Res 2010; 38:e200) Amplicons are gel purified and purified amplicons are pooled in equal amounts for sequencing. Paired-end sequencing is performed by UMGC at a read length of 300 nt using the Illumina MiSeq platform (Illumina, Inc., San Diego, Calif., USA). Sequencing data are recovered as fastq files and are deposited in the Sequence Read Archive of the National Center for Biotechnology Information under BioProject accession numbers SRP071210 and SRP064361, for germ-free mice and donor/patient samples, respectively.

Sequence processing and analysis, unless otherwise noted, is performed using MOTHUR ver. 1.34.0. (Schloss et al. Appl. Environ. Microbiol. 2009; 75:7537-41, Staley et al. Jmicrobiol Methods 2015; 114:43-50). Fastq files for both forward and reverse reads are trimmed to 150 nt and paired-end joined using fastq-join software. (Aronesty Open Bioinforma J 201; 7:1-8). Sequences are quality trimmed at an average quality score of 35 over a window of 50 nt. Any sequence with homopolymers >8 nt, an ambiguous base, or >2 mismatches from primer sequences is excluded. High-quality sequences are aligned against the SILVA database ver. 119 (Pruesse E et al. Nucleic Acids Res 2007; 35:7188-96) and subjected to a 2% pre-clustering step. (Huse et al. Environ Microbiol 2010; 12:1889-98). Chimeras are identified and removed using UCHIME software. (Edgar et al. Bioinformatics 2011; 27:2194-200). For comparison between samples, the number of reads per sample is rarefied to 50,456 reads for germ-free mice and 11,500 for patient comparisons. (Gihring et al. Environ Microbiol 2012; 14:285-90). Operational taxonomic units (OTUs) are assigned at 97% identity using the furthest-neighbor algorithm and taxonomic assignments are made against the RDP14 database. (Cole et al. Nucleic Acids Res 2009; 37:D141-5). Donor community engraftment is determined as a percentage of recipient communities that could be attributed to donor samples using the default parameters of the SourceTracker software. (Knights et al. Nat. Methods 2011; 8:761-3)

Figure 3A:
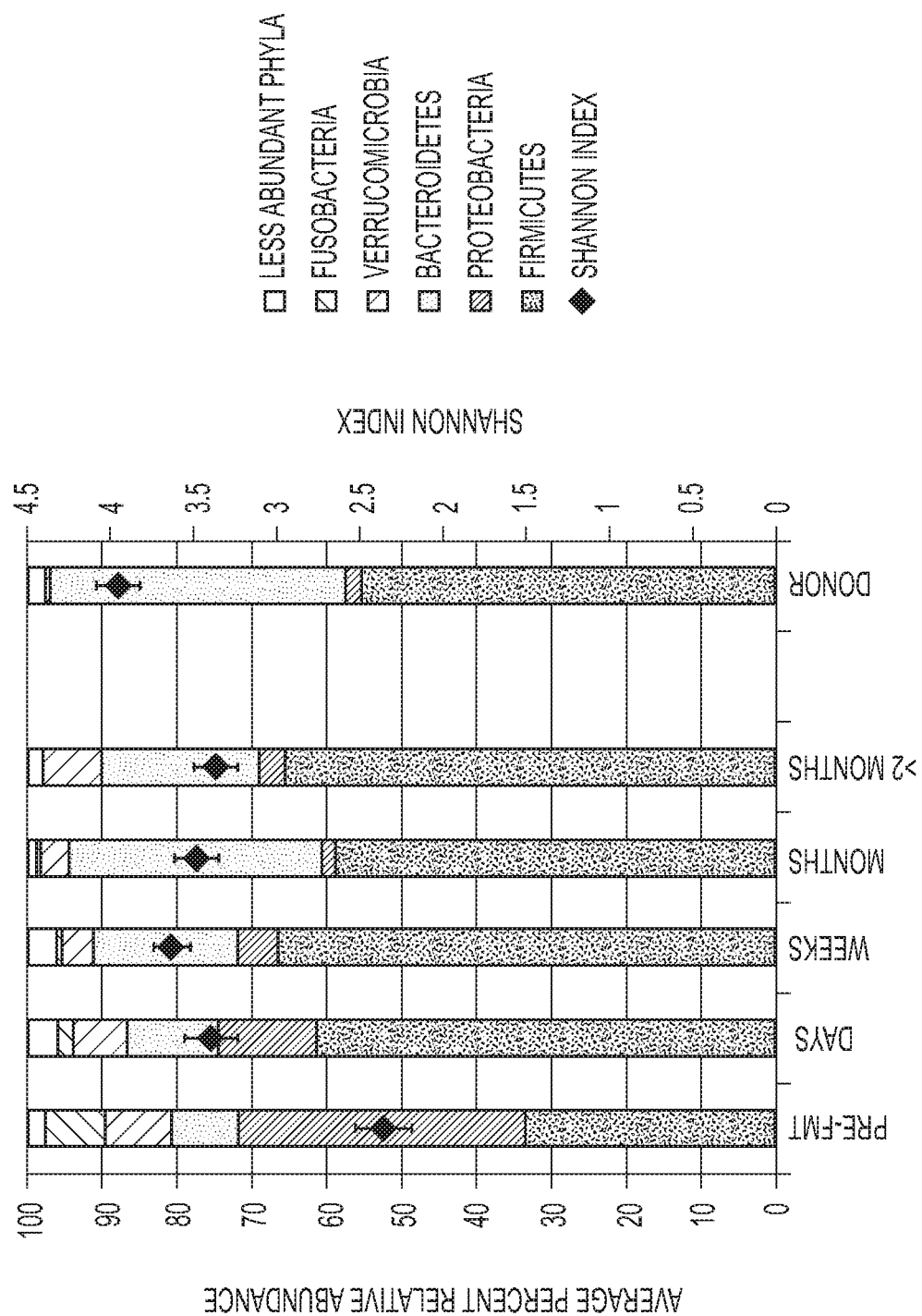
FIG. 3A shows the distribution of phyla in cured patient and donor samples in accordance with Example 5 of the present disclosure.
Figure 3B:
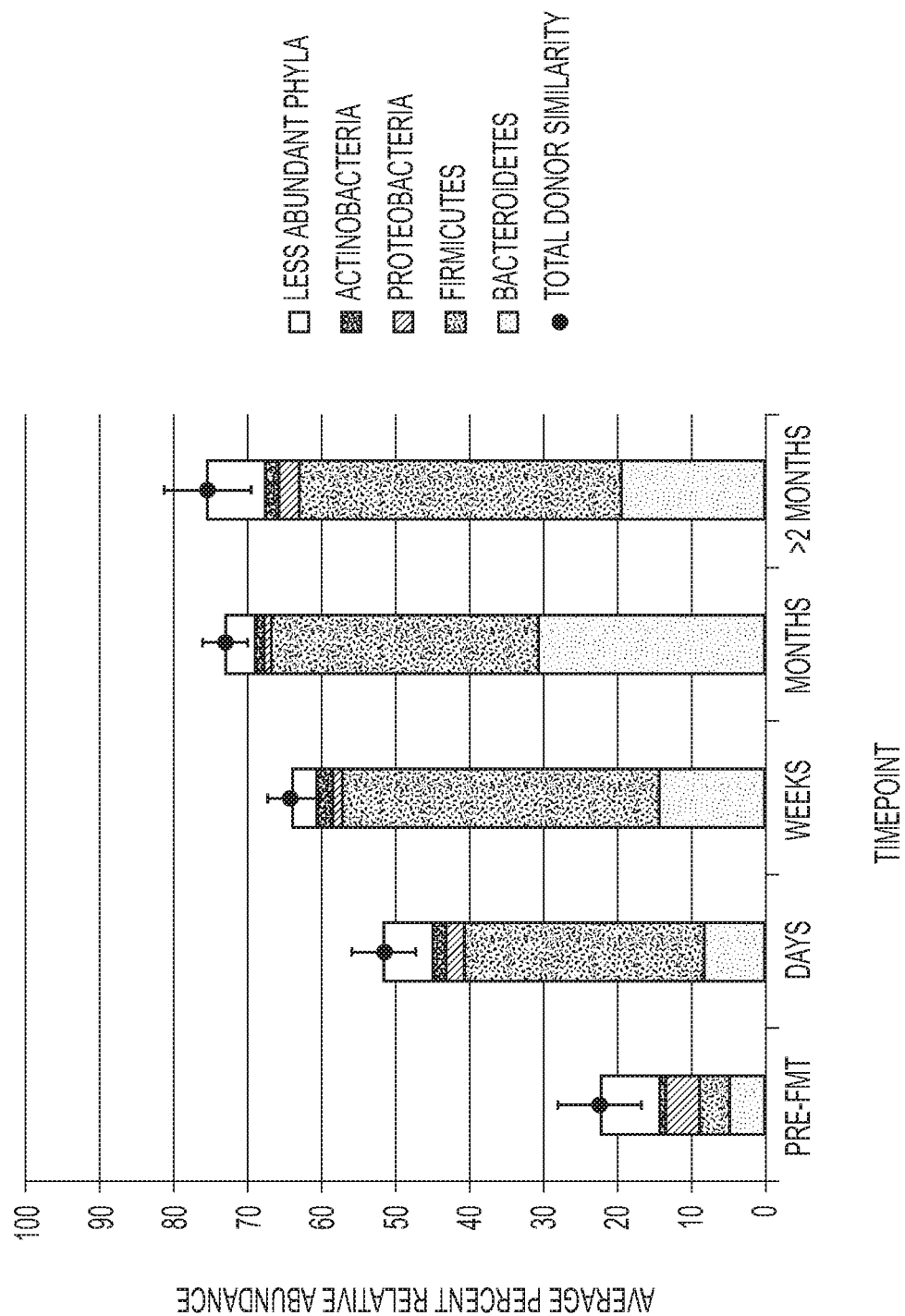
FIG. 3B shows the phylum-level classification of OTUs that were associated with donor contribution in accordance with Example 5 of the present disclosure.

In order to simplify the analysis, the characterization of the fecal microbiome is limited to samples obtained from patients for whom the capsule treatment is their first FMT. All samples prior to FMT show markedly lower microbial diversity compared to the donor microbiota (Table 4). Similar to previous investigations of patients undergoing FMT for R-CDI in this own program and others (van Nood et al. N. Engl. J. Med. 2013; 368:407-15; Hamilton et al. Gut Microbes 2013; 4:125-35; Weingarden et al Microbiome 2015; 3:10; Weingarden et al. Am J Physiol Gastrointest Liver Physiol 2014; 306:G310-9; Shankar et al. Microbiome 2014; 2:13; Shahinas et al. Mbio 2012; 3; Seekatz et al. MBio 2014; 5:e00893-14), these pre-FMT samples demonstrate markedly increased relative abundance of *Proteobacteria* (40.7±4.3% versus 2.0±0.5%, p<0.001) and a reduction in the relative abundances of *Firmicutes* (34.4±3.8% versus 55.4±3.3%, p=0.443) and *Bacteroidetes* (8.5±2.7% versus 39.7±3.4%, p<0.001) compared to the donor samples. Capsule FMT is associated with increased microbial diversity, contraction of relative abundance of *Proteobacteria*, and an increase in the relative abundances of *Firmicutes* and *Bacteroidetes*, discussed in detail below. Interestingly, the kinetics of these changes is not equivalent among different phyla. FIG. 3A shows the distribution of phyla in cured patient and donor samples. Samples are collected prior to FMT (pre-FMT), within the first 6 days post-FMT (days), between 7 and 21 days post-FMT (weeks), between 30 and 60 days post-FMT (months), or after 2 months post-FMT (>2 months). FIG. 3B shows the phylum-level classification of OTUs that are associated with donor contribution. Error bars reflect standard error of the mean. In particular, the recovery of *Bacteroidetes* is somewhat delayed and its relative abundance do not stabilize until after one month following capsule FMT.

TABLE 4

Alpha diversity indices (mean ± SE) for microbial communities in patient samples.

| Clinical Outcome | Timepoint* | N (individuals) | n (sample) | Shannon |
|---|---|---|---|---|
| Donor | Donor | 3 | 5 | 3.95 ± 0.13 |
| Cure | pre-FMT | 26 | 28 | 2.36 ± 0.17 |
|  | Days | 25 | 25 | 3.40 ± 0.16 |
|  | Weeks | 27 | 34 | 3.63 ± 0.11 |
|  | Months | 11 | 14 | 3.48 ± 0.13 |
|  | >2 months | 7 | 7 | 3.37 ± 0.13 |
| Recurrence | pre-FMT | 8 | 10 | 2.97 ± 0.44 |
|  | Days | 8 | 9 | 3.36 ± 0.40 |
|  | Weeks | 8 | 11 | 3.39 ± 0.38 |
|  | Months | 4 | 4 | 3.27 ± 0.22 |
|  | >2 months | 2 | 2 | 2.94 ± 0.97 |
|  | p-value |  |  | <0.0001 |

In order to assess the contribution of donor microbiota engraftment to the changes in the FMT-associated microbial community structure, the SourceTracker computer program is employed. Prior to FMT this analysis attributes a relatively low fraction (22.6±4.4%) of OTUs to the donors in patient samples. Donor similarity increases at all time points after capsule FMT and is greatest at least one month following treatment. Analysis of fecal samples from patients that received high dose capsule FMT ($1.25$-$2.5 \times 10^{12}$ bacteria) versus low dose ($2.1$-$2.5 \times 10^{11}$ bacteria) do not show any dose-dependent differences in microbial diversity changes or kinetics of engraftment, further discussed in supplementary results. Similarly, the microbiome analysis does not show any deleterious effect of proton pump inhibitors on capsule FMT). Finally, the fecal samples from all patients that failed to clear CDI with one capsule FMT is analyzed, as discussed further below. Following FMT, the microbiomes of these patients generally become taxonomically more similar to donors, except the one who receives antibiotics shortly following the treatment. However, the small number of patients precludes elucidation of a clear pattern predictive of FMT failure.

Figure 4:
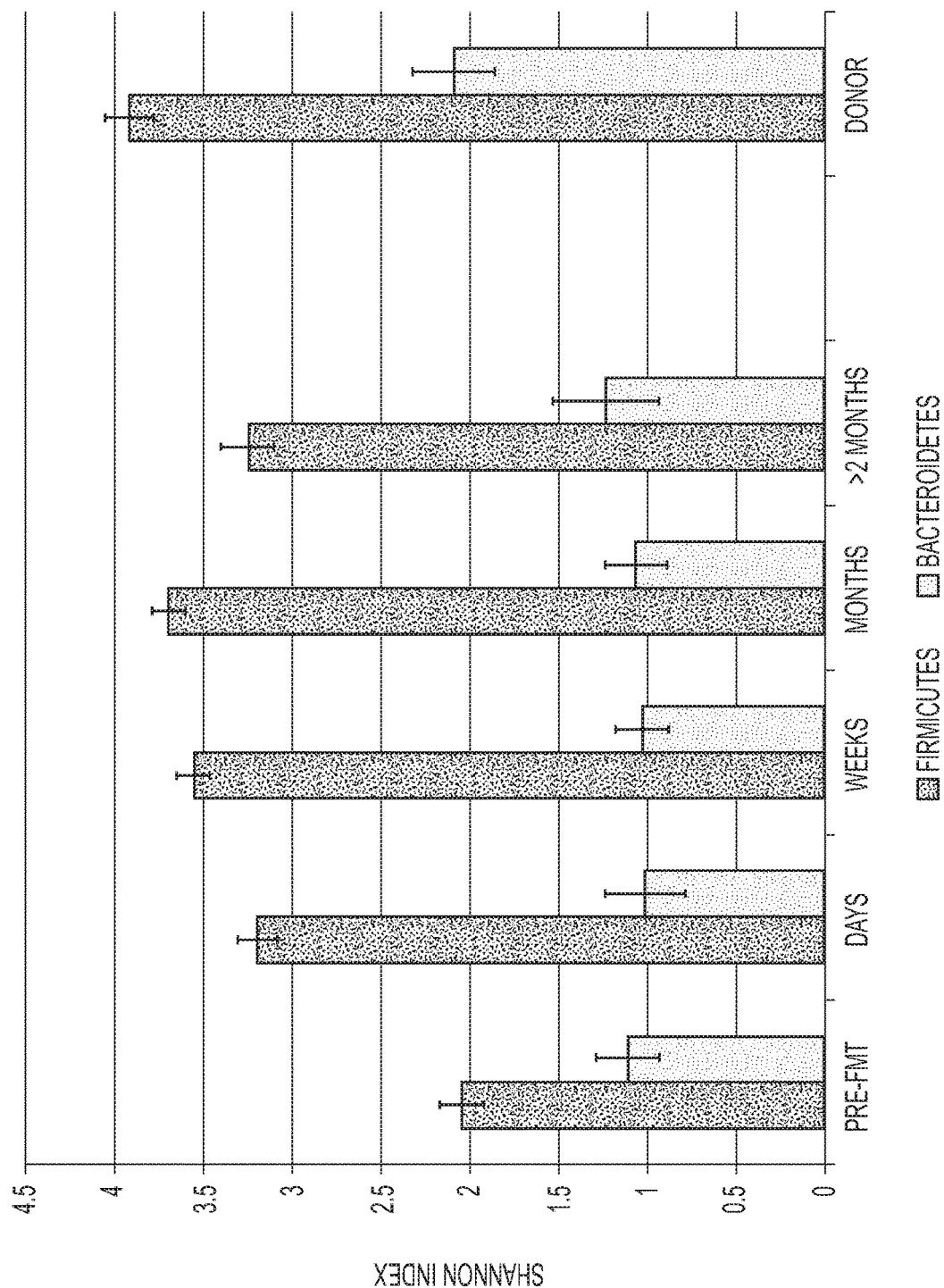
FIG. 4 shows the alpha diversity within the *Bacteroidetes* and *Firmicutes* phyla, individually, in patients pre- and post-FMT cured by FMT, and the donor samples in accordance with Example 5 of the present disclosure.

Among all donor and patient samples, a mean sample coverage of 99.1±0.1% is observed with a mean of 279±29 OTUs observed in each sample. Alpha diversity is significantly lower in pre-FMT patient samples than donor and post-FMT samples, regardless of clinical outcome, based on the Shannon index (Table 4, p<0.0001). While the abundance of *Firmicutes* does not differ significantly following capsule FMT, alpha diversity within the *Firmicutes* is significantly lower in pre-FMT samples and those from patients who experienced recurrence (FIG. 4, p<0.0001), but differences in alpha diversity within the *Bacteroidetes*, which does show significant differences in abundance, did not differ significantly (p=0.468)

Figure 5:
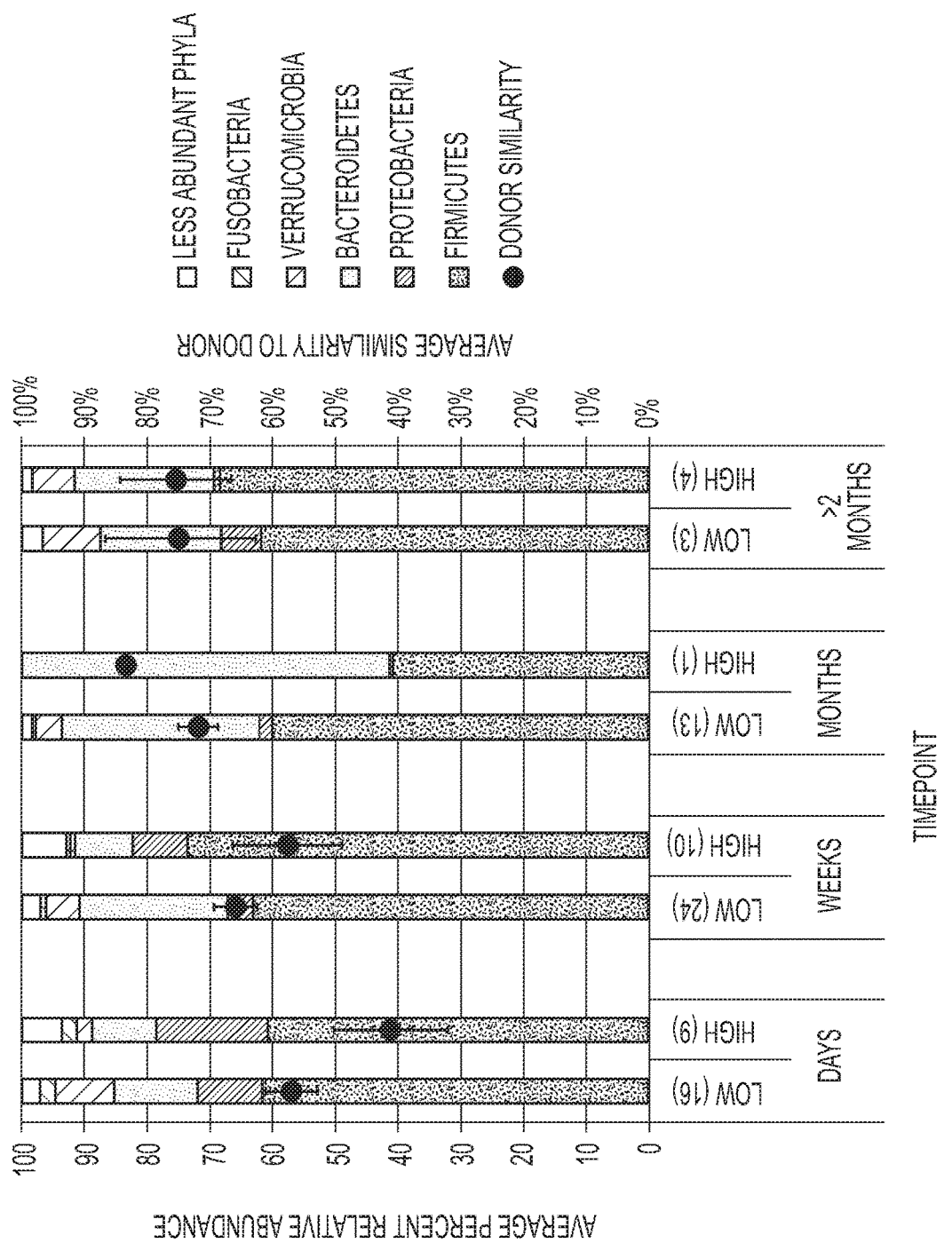
FIG. 5 shows the distribution of phyla and similarity to donor (i.e., attribution of DNA sequences to donor engraftment, as determined by using the SourceTracker software package) among samples from patients administered low ($2.1$-$2.5 \times 10^{11}$ cells) and high ($1.25$-$2.5 \times 10^{12}$ cells) doses of capsule FMT in accordance with Example 5 of the present disclosure.
Figure 6:
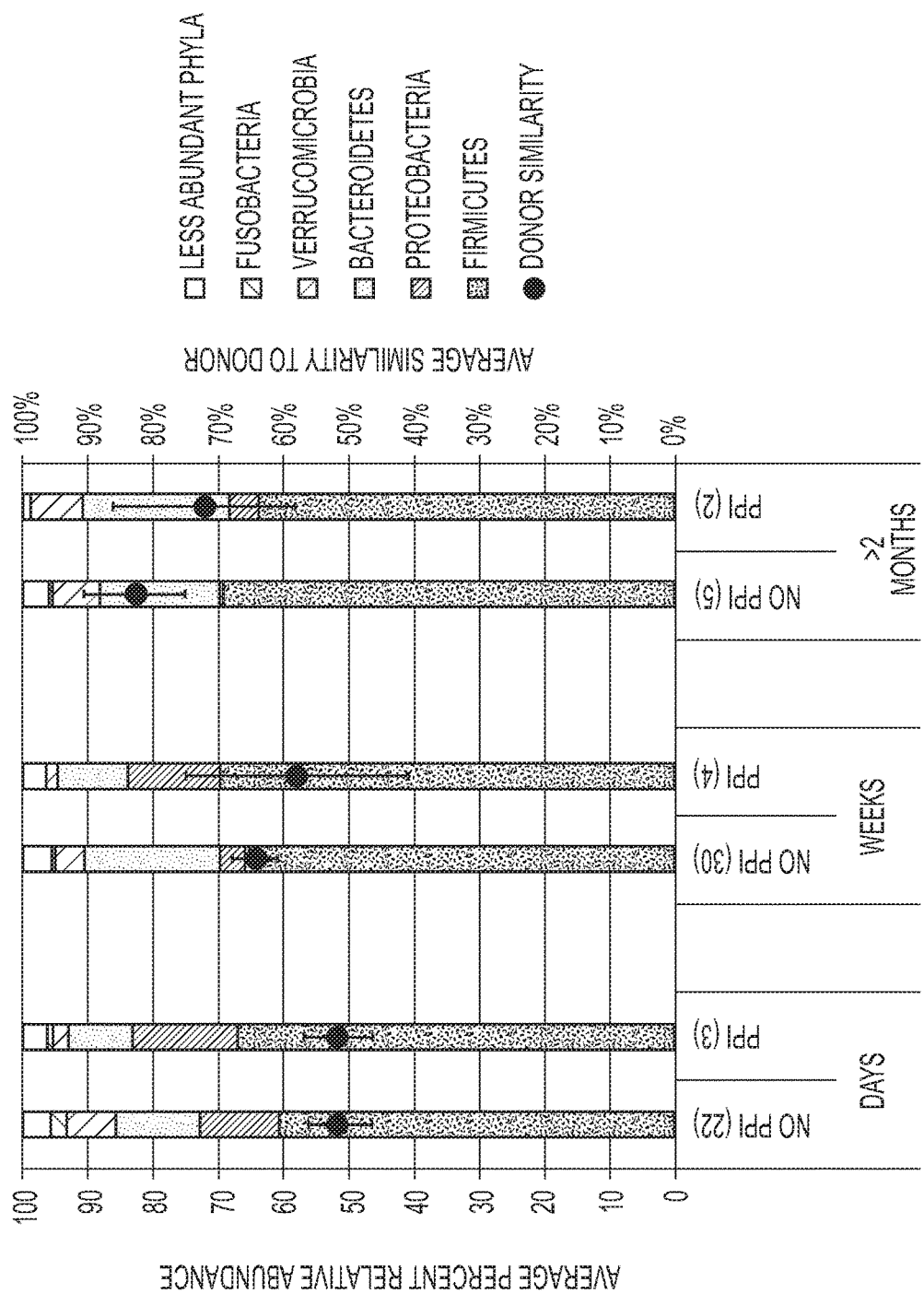
FIG. 6 shows the distribution of phyla and total donor similarity among samples from patients grouped by use of PPI in accordance with Example 5 of the present disclosure.

Capsule dosage does not significantly affect alpha diversity as measured by the Shannon index, with no significant differences between patients who received $10^{11}$ bacteria dosages (3.42±0.07) compared to $10^{12}$ bacteria (3.72±0.18, p=0.187). Despite some variation in the relative abundances of the predominant phyla (FIG. 5), capsule dosage also does not significantly affect relative abundances of phyla within single timepoints (p>0.05). Similarly, the extent of engraftment, measured by SourceTracker, is not dose-dependent, with no differences in the percent of donor similarity at any timepoint (p>0.920). Furthermore, following the two-month follow-up, patient communities and donor similarity are nearly identical regardless of dose. Similar to differences in dosage, Shannon diversity is not significantly affected by the use of proton pump inhibitors (PPI), with mean indices of 3.51±0.08 versus 3.50±0.10, for those on and off PPI, respectively (p=0.824). Use of PPI also does not significantly affect the relative abundances of major phyla (FIG. 6, p>0.05) or the extent of donor engraftment (p>0.977) within a single timepoint.

Figure 7A:
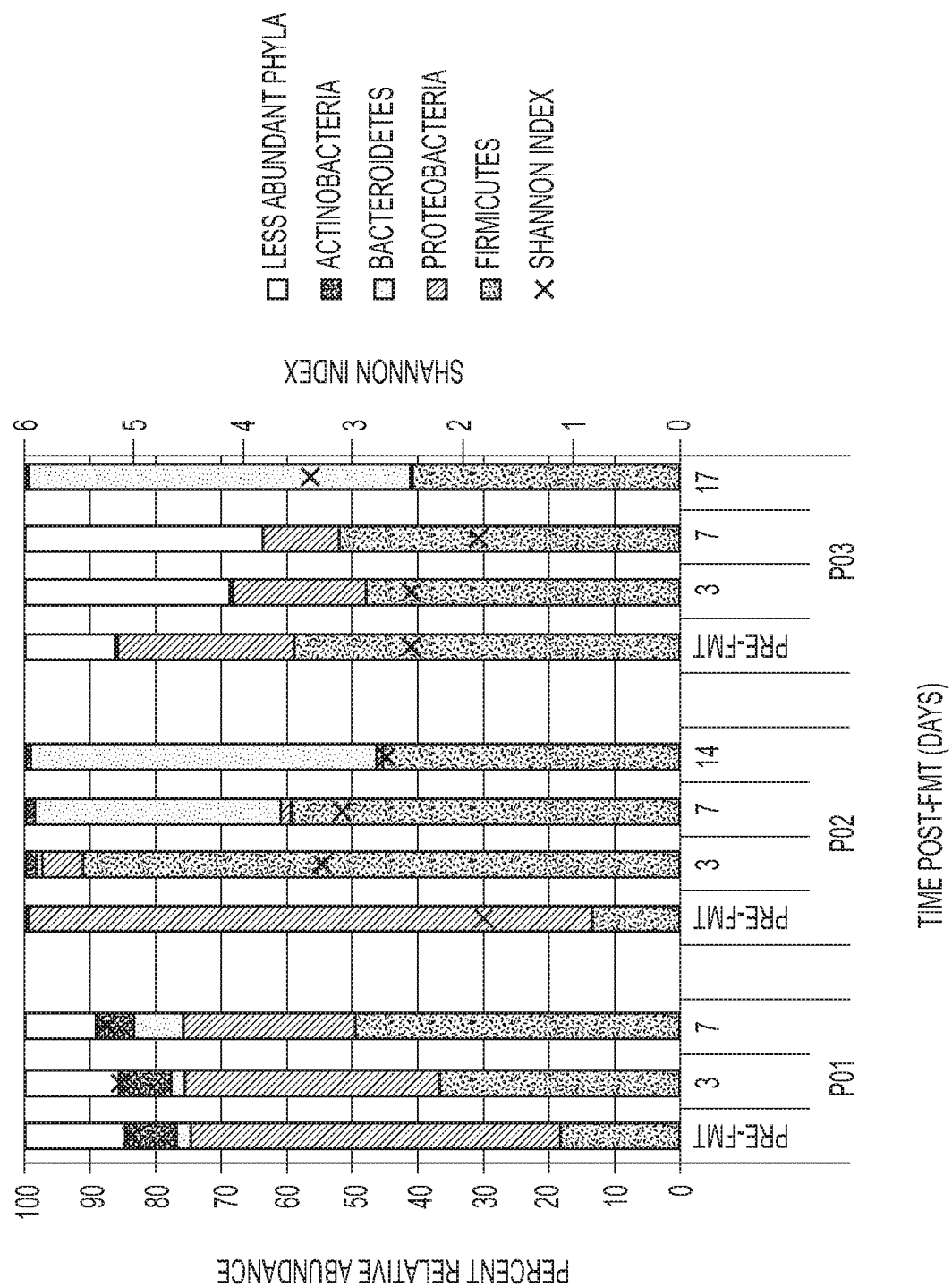
FIG. 7A shows the distribution of phyla and alpha diversity among patients who experienced recurrence of *C. difficile* infection following initial capsule FMT in accordance with Example 5 of the present disclosure.
Figure 7B:
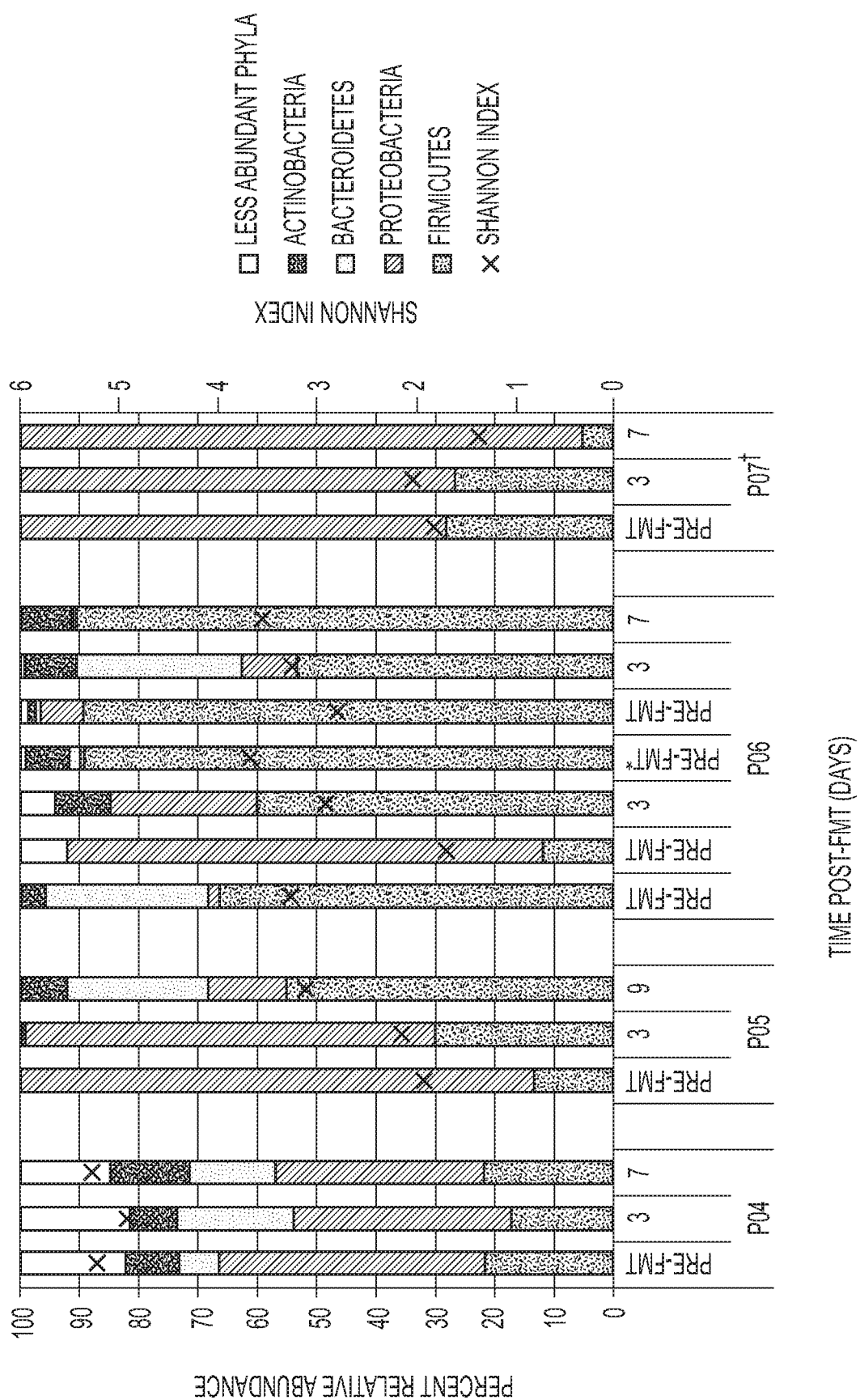
FIG. 7B shows the distribution of phyla and alpha diversity among patients who experienced recurrence of *C. difficile* infection following capsule FMT following recurrence after colonoscopic FMT in accordance with Example 5 of the present disclosure.

Patients who experienced recurrence show similar taxonomic composition prior to FMT (FIG. 7), but the abundance of *Proteobacteria* in the days following FMT is observed to be greater than among patients who did not relapse (p=0.013). While the microbiomes of several patients (i.e. P02, P03, and P05) return to donor-like assemblages primarily comprised of *Firmicutes* and *Bacteroidetes*, communities also show decreases in alpha diversity within the first weeks following FMT, while other patients maintained a greater proportion of *Proteobacteria*. Notably, the microbiome of the patient who is placed on antibiotics for UTI (P07) was primarily comprised of *Proteobacteria*. Thus, a clear trend in the shifts in microbial community composition that might indicate failure of FMT require further investigation.

The invention claimed is:

1. A method for treating a *Clostridium difficile* infection (CDI) in a subject in need thereof, said method comprising orally administering to said subject a single dose of a pharmaceutical composition comprising a freeze-dried fecal microbe preparation, wherein said single dose is administered within one day and said single dose is capable of achieving a CDI clearance rate of at least 80%.

2. The method of claim 1, wherein said CDI clearance rate is calculated based on a patient population size of 20, 30, 40, 50, or 100.

3. The method of claim 1, wherein the relative abundance of *Proteobacteria* in said subject's stool decreases by at least 50% within 3 to 6 days from administering said single dose relative to a baseline abundance immediately prior to administering said single dose.

4. The method of claim 1, wherein the relative abundance of one or more bacteria selected from the group consisting of *Firmicutes* and *Bacteroidetes* in said subject's stool increases by at least 50% within 3 to 6 days from administering said single dose relative to a baseline abundance immediately prior to administering said single dose.

5. The method of claim 1, wherein the alpha diversity within *Firmicutes* in said subject's stool increases by at least 100% within 3 to 6 days from administering said single dose relative to a baseline diversity immediately prior to administering said single dose.

6. The method of claim 1, wherein the alpha diversity within *Bacteroidetes* in said subject's stool remains substantially unchanged within 6 days, 21 days, or 60 days from administering said single dose relative to a baseline diversity immediately prior to administering said single dose.

7. The method of claim 1, wherein said single dose achieves a CDI clearance rate of at least 90%.

8. The method of claim 1, wherein said subject is allowed only water for two hours prior to said administering said pharmaceutical composition, is allowed only water for two hours after said administering said pharmaceutical composition, or both.

9. The method of claim 1, wherein said subject experience little or no bowel movement irregularity, bloating, or flatulence within the first two weeks from administering said single dose.

10. The method of claim 1, wherein said pharmaceutical composition is capable of being stored at room temperature for at least 3 days prior to said administering.

11. The method of claim 1, wherein said method requires no colon purgative prior to administering said single dose.

12. The method of claim 1, wherein said pharmaceutical composition is formulated as an enteric coated capsule or microcapsule, an acid-resistant capsule or microcapsule, an enteric coated tablet, an acid-resistant tablet, an enteric coated geltab, an acid-resistant geltab, an enteric coated pill, or an acid-resistant pill.

13. The method of claim 1, wherein said single dose comprises a total cell count of $10^{10}$ or greater.

14. The method of claim 1, wherein said freeze-dried fecal microbe preparation comprises a cryoprotectant selected from the group consisting of trehalose, glucose, fructose, sucrose, lactose, ribose, mannitol, erythritol, arabitol, sorbitol, alanine, glycine, proline, sand a combination thereof.

15. The method of claim 1, wherein said CDI is primary CDI or recurrent CDI.

16. The method of claim 1, wherein said fecal microbe preparation comprises a donor's entire or substantially complete microbiota.

17. The method of claim 1, wherein the preparation of said fecal microbe preparation involves a separation step selected from the group consisting of filtering, sieving, differential centrifugation, density gradient centrifugation, filtration, chromatography, and a combination thereof.

18. The method of claim 1, wherein said fecal microbe preparation comprises a preparation of viable flora in proportional content that resembles a normal healthy human fecal flora.

19. The method of claim 1, wherein said subject is pretreated with an antibiotic prior to administration of said composition.

20. The method of claim 19, wherein said antibiotic is selected from the group consisting of amoxicillin, tetracycline, metronidazole, rifabutin, clarithromycin, clofazimine, vancomycin, rifampicin, nitroimidazole, chloramphenicol, and a combination thereof.

* * * * *